United States Patent
Bonutti

(10) Patent No.: US 9,770,238 B2
(45) Date of Patent: *Sep. 26, 2017

(54) MAGNETIC POSITIONING APPARATUS

(75) Inventor: Peter M. Bonutti, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 1 day.

This patent is subject to a terminal disclaimer.

(21) Appl. No.: 10/784,401

(22) Filed: Feb. 23, 2004

(65) Prior Publication Data

US 2004/0167548 A1    Aug. 26, 2004

Related U.S. Application Data

(63) Continuation of application No. 10/005,652, filed on Dec. 3, 2001, now Pat. No. 6,719,765.

(51) Int. Cl.
*A61B 17/04* (2006.01)

(52) U.S. Cl.
CPC .......... *A61B 17/0401* (2013.01); *A61B 17/04* (2013.01); *A61B 17/0469* (2013.01); *A61B 2017/0414* (2013.01)

(58) Field of Classification Search
CPC . A61B 17/04; A61B 17/0401; A61B 17/0469; A61B 2017/0414
USPC .......... 606/22–227, 232; 600/9, 11–14, 104, 600/141, 142, 562, 12.13; 433/4; 294/99.2; 81/418, 176.3, 119, 300, 318
See application file for complete search history.

(56) References Cited

U.S. PATENT DOCUMENTS

| | | |
|---|---|---|
| 157,343 A | 12/1874 | Molesworth |
| 319,296 A | 6/1885 | Molesworth |
| 668,878 A | 2/1901 | Jensen |
| 668,879 A | 2/1901 | Miller |
| 673,783 A | 5/1901 | Peters |
| 702,789 A | 6/1902 | Gibson |

(Continued)

FOREIGN PATENT DOCUMENTS

| | | |
|---|---|---|
| CA | 2641580 | 8/2007 |
| CA | 2680827 | 9/2008 |

(Continued)

OTHER PUBLICATIONS

Arnold RW, Erie JC. Magnetized forceps for metallic corneal foreign bodies. Arch Ophthalmol 1988;106(11):1502. USA.

(Continued)

*Primary Examiner* — Julian W Woo

(57) ABSTRACT

The present invention relates to an instrument and method for passing a medical implement through tissue with magnetic forces. The implement can be an implant, either permanent or temporary, and is provided with a magnetic component. A magnetic field is established and the magnetic component and/or magnetic field is manipulated to drive the implant through tissue. Alternatively, the instrument itself is the implement and includes at least one magnetic element so that a magnetic field established by an external magnetic generator drives the instrument through tissue. In another embodiment, the instrument includes two magnetic elements that are moveable with respect to one another and interaction between the magnetic elements drives the instrument through the tissue. Examples of applications of the present invention include a suture passer and a tissue anchor.

41 Claims, 6 Drawing Sheets

(56) References Cited

U.S. PATENT DOCUMENTS

| | | |
|---|---|---|
| 832,201 A | 10/1906 | Kistler |
| 862,712 A | 8/1907 | Collins |
| 1,213,005 A | 1/1917 | Pillsbury |
| 1,433,031 A | 10/1922 | Pegaitaz |
| 1,725,670 A | 8/1929 | Novack |
| 1,863,057 A | 6/1932 | Innes |
| 1,870,942 A | 8/1932 | Beatty |
| 2,121,193 A | 12/1932 | Hanicke |
| 1,909,967 A | 5/1933 | Jones |
| 1,959,615 A | 5/1934 | Derrah |
| 2,187,852 A | 8/1936 | Friddle |
| 2,178,840 A | 11/1936 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,433,815 A | 12/1947 | Nicephore et al. |
| 2,518,276 A | 8/1950 | Braward |
| 2,526,662 A | 10/1950 | Hipps et al. |
| 2,557,669 A | 6/1951 | Lloyd |
| 2,566,221 A | 8/1951 | Lovell |
| 2,566,499 A | 9/1951 | Richter |
| 2,589,720 A | 3/1952 | McMath |
| 2,621,145 A | 12/1952 | Sano |
| 2,621,653 A | 12/1952 | Briggs |
| 2,642,874 A | 6/1953 | Keeling |
| 2,687,719 A | 8/1954 | Hoyt |
| 2,701,559 A | 2/1955 | Cooper |
| 2,724,326 A | 11/1955 | Long |
| 2,725,053 A | 11/1955 | Bambara |
| 2,830,587 A | 4/1958 | Everett |
| 2,854,983 A | 10/1958 | Baskin |
| 2,936,760 A | 5/1960 | Gants |
| 2,955,530 A | 10/1960 | Nilo |
| 3,039,468 A | 6/1962 | Price |
| 3,048,522 A | 8/1962 | Velley |
| 3,081,773 A | 3/1963 | Boyd |
| 3,108,357 A | 10/1963 | Liebig |
| 3,108,595 A | 10/1963 | Overment |
| 3,204,635 A | 9/1965 | Voss et al. |
| 3,229,006 A | 1/1966 | Nohl |
| 3,253,594 A | 5/1966 | Matthews et al. |
| 3,347,234 A | 10/1967 | Voss |
| 3,367,809 A | 2/1968 | Soloff |
| 3,391,690 A * | 7/1968 | Armao .................. 600/564 |
| 3,397,699 A | 8/1968 | Kohl |
| 3,417,745 A | 12/1968 | Sheldon |
| 3,459,175 A | 8/1969 | Miller |
| 3,469,003 A | 9/1969 | Hardy |
| 3,477,429 A | 11/1969 | Sampson |
| 3,495,586 A | 2/1970 | Regenbogen |
| 3,508,444 A | 4/1970 | Leis |
| 3,513,848 A | 5/1970 | Winston et al. |
| 3,514,791 A | 6/1970 | Sparks |
| 3,517,128 A | 6/1970 | Hines |
| 3,518,993 A | 7/1970 | Blake |
| 3,554,192 A | 1/1971 | Isberner |
| 3,557,794 A | 1/1971 | Patten |
| 3,577,991 A * | 5/1971 | Wilkinson ............... 606/206 |
| 3,593,709 A | 7/1971 | Halloran |
| 3,596,292 A | 8/1971 | Erb et al. |
| 3,608,539 A | 9/1971 | Miller |
| 3,613,497 A | 10/1971 | Heldermann |
| 3,620,218 A | 11/1971 | Schmitt |
| 3,624,747 A | 11/1971 | McKnight et al. |
| 3,625,220 A | 12/1971 | Engelsher |
| 3,626,949 A | 12/1971 | Shute |
| 3,635,223 A | 1/1972 | Klieman |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,670,732 A | 6/1972 | Robinson |
| 3,678,980 A | 7/1972 | Gutshall |
| 3,698,017 A | 10/1972 | Scales et al. |
| 3,709,218 A | 1/1973 | Halloran |
| 3,711,347 A | 1/1973 | Wagner et al. |
| 3,716,051 A | 2/1973 | Fischer |
| 3,721,244 A | 3/1973 | Elmaleh |
| 3,739,773 A | 6/1973 | Schmitt et al. |
| 3,750,652 A | 8/1973 | Sherwin |
| 3,760,808 A | 9/1973 | Bleuer |
| 3,769,980 A | 11/1973 | Karman |
| 3,774,244 A | 11/1973 | Walker |
| 3,774,596 A | 11/1973 | Cook |
| 3,777,538 A * | 12/1973 | Weatherly .......... A61B 17/1285 606/142 |
| 3,779,239 A | 12/1973 | Fischer et al. |
| 3,788,318 A | 1/1974 | Kim et al. |
| 3,789,852 A | 2/1974 | Kim et al. |
| 3,800,788 A | 4/1974 | White |
| 3,802,438 A | 4/1974 | Wolvek |
| 3,804,089 A | 4/1974 | Bridgman |
| 3,807,393 A | 4/1974 | McDonald |
| 3,807,394 A | 4/1974 | Attenborough |
| 3,809,075 A | 5/1974 | Matles |
| 3,811,449 A | 5/1974 | Gravlee et al. |
| 3,812,855 A | 5/1974 | Banko |
| 3,815,963 A | 6/1974 | Wilk |
| 3,825,010 A | 7/1974 | McDonald |
| 3,833,003 A | 9/1974 | Taricco |
| 3,835,849 A | 9/1974 | McGuire |
| 3,841,304 A | 10/1974 | Jones |
| 3,842,824 A | 10/1974 | Neufeld |
| 3,845,772 A | 11/1974 | Smith |
| 3,850,172 A | 11/1974 | Cazalis |
| 3,850,720 A | 11/1974 | Collins |
| 3,852,830 A | 12/1974 | Marmor |
| 3,857,396 A | 12/1974 | Hardwick |
| 3,863,639 A | 2/1975 | Kleaveland |
| 3,867,932 A | 2/1975 | Huene |
| 3,869,731 A | 3/1975 | Waugh et al. |
| 3,874,264 A | 4/1975 | Polos |
| 3,875,652 A | 4/1975 | Arnold |
| 3,875,946 A | 4/1975 | Duncan |
| 3,882,852 A | 5/1975 | Sinnreich |
| 3,889,686 A | 6/1975 | Duturbure |
| 3,894,530 A | 7/1975 | Dardik et al. |
| 3,898,992 A | 8/1975 | Balamuth |
| 3,903,549 A | 9/1975 | Deyerle |
| 3,911,923 A | 10/1975 | Yoon |
| 3,915,171 A | 10/1975 | Shermeta |
| 3,918,442 A | 11/1975 | Nikolaev et al. |
| 3,920,022 A | 11/1975 | Pastor |
| 3,939,835 A | 2/1976 | Bridgman |
| 3,945,375 A | 3/1976 | Banko |
| 3,960,143 A | 6/1976 | Terada |
| 3,961,632 A | 6/1976 | Moossun |
| 3,967,625 A | 7/1976 | Yoon |
| 3,968,800 A | 7/1976 | Vilasi |
| 3,970,089 A | 7/1976 | Saice |
| 3,973,277 A | 8/1976 | Semple et al. |
| 3,976,079 A | 8/1976 | Samuels et al. |
| 3,989,049 A | 11/1976 | Yoon |
| 3,991,426 A | 11/1976 | Flom et al. |
| 3,994,287 A | 11/1976 | Turp et al. |
| 4,000,525 A | 1/1977 | Klawitter et al. |
| 4,022,216 A | 5/1977 | Stevens |
| 4,023,559 A | 5/1977 | Gaskell |
| 4,024,588 A | 5/1977 | Janssen |
| 4,040,413 A | 8/1977 | Ohshiro |
| 4,053,953 A | 10/1977 | Flom et al. |
| 4,055,862 A | 11/1977 | Farling |
| 4,057,369 A | 11/1977 | Isenberg |
| 4,064,566 A | 12/1977 | Fletcher et al. |
| 4,077,412 A | 3/1978 | Moossun |
| 4,081,866 A | 4/1978 | Upshaw et al. |
| 4,083,369 A | 4/1978 | Sinnreich |
| 4,085,466 A | 4/1978 | Goodfellow et al. |
| 4,085,743 A | 4/1978 | Yoon |
| 4,089,071 A | 5/1978 | Kainberz et al. |
| 4,092,113 A | 5/1978 | Hardy |
| 4,103,680 A | 8/1978 | Yoon |
| 4,122,605 A | 10/1978 | Hirabayashi et al. |

(56) References Cited

U.S. PATENT DOCUMENTS

| | | | |
|---|---|---|---|
| 4,122,856 A * | 10/1978 | Mosior | A61B 17/32001 606/170 |
| 4,142,517 A | 3/1979 | Contreras Guerrero de Stavropoulos et al. | |
| 4,148,307 A | 4/1979 | Utsugi | |
| 4,156,574 A | 5/1979 | Boden | |
| 4,164,794 A | 8/1979 | Spector et al. | |
| 4,169,470 A | 10/1979 | Ender et al. | |
| 4,171,544 A | 10/1979 | Hench et al. | |
| 4,177,814 A | 12/1979 | Knepshield et al. | |
| 4,183,102 A | 1/1980 | Guiset | |
| 4,186,448 A | 2/1980 | Brekke | |
| 4,191,747 A | 3/1980 | Scheicher | |
| 4,198,981 A | 4/1980 | Sinnreich | |
| 4,199,864 A | 4/1980 | Ashman | |
| 4,200,939 A | 5/1980 | Oser | |
| 4,203,444 A | 5/1980 | Bonnell et al. | |
| 4,209,012 A | 6/1980 | Smucker | |
| 4,209,861 A | 7/1980 | Walker et al. | |
| 4,210,148 A | 7/1980 | Stivala | |
| 4,210,580 A | 7/1980 | Amrani | |
| 4,213,209 A | 7/1980 | Insall et al. | |
| 4,213,816 A | 7/1980 | Morris | |
| 4,224,696 A | 9/1980 | Murray et al. | |
| 4,224,929 A | 9/1980 | Furihata | |
| 4,228,802 A | 10/1980 | Trott | |
| 4,230,119 A | 10/1980 | Blum | |
| 4,235,233 A | 11/1980 | Mouwen | |
| 4,235,238 A | 11/1980 | Ogiu et al. | |
| 4,240,433 A | 12/1980 | Bordow | |
| 4,243,048 A | 1/1981 | Griffin | |
| 4,244,370 A | 1/1981 | Furlow et al. | |
| 4,257,411 A | 3/1981 | Cho | |
| 4,263,900 A | 4/1981 | Nicholson | |
| 4,265,231 A | 5/1981 | Scheller, Jr. et al. | |
| 4,265,848 A | 5/1981 | Rusch | |
| 4,271,848 A | 6/1981 | Turner | |
| 4,274,414 A | 6/1981 | Johnson et al. | |
| 4,281,649 A | 8/1981 | Derweduwen | |
| 4,291,698 A | 9/1981 | Fuchs | |
| 4,295,464 A | 10/1981 | Shihata | |
| 4,298,002 A | 11/1981 | Ronel et al. | |
| 4,298,992 A | 11/1981 | Burstein et al. | |
| 4,298,998 A | 11/1981 | Naficy | |
| 4,299,224 A | 11/1981 | Noiles | |
| 4,299,227 A | 11/1981 | Lincoff | |
| 4,304,178 A | 12/1981 | Haberle | |
| 4,309,488 A | 1/1982 | Heide et al. | |
| 4,311,145 A | 1/1982 | Esty et al. | |
| 4,312,353 A | 1/1982 | Shahbabian | |
| 4,320,762 A | 3/1982 | Bentov | |
| 4,344,193 A | 8/1982 | Kenny | |
| 4,349,029 A | 9/1982 | Mott | |
| 4,349,921 A | 9/1982 | Kuntz | |
| 4,351,069 A | 9/1982 | Ballintyn et al. | |
| 4,352,883 A | 10/1982 | Lim | |
| 4,357,940 A | 11/1982 | Muller | |
| 4,364,381 A | 12/1982 | Sher et al. | |
| 4,365,356 A | 12/1982 | Broemer et al. | |
| 4,369,768 A | 1/1983 | Vukovic | |
| 4,373,217 A | 2/1983 | Draenert | |
| 4,373,709 A | 2/1983 | Whitt | |
| 4,374,523 A | 2/1983 | Yoon | |
| 4,385,404 A | 5/1983 | Sully et al. | |
| 4,388,921 A | 6/1983 | Sutter et al. | |
| 4,391,909 A | 7/1983 | Lim | |
| 4,395,798 A | 8/1983 | McVey | |
| 4,400,833 A | 8/1983 | Kurland | |
| 4,407,273 A | 10/1983 | Ouchi | |
| 4,409,974 A | 10/1983 | Freedland | |
| 4,414,166 A | 11/1983 | Charlson et al. | |
| 4,421,112 A | 12/1983 | Mains et al. | |
| 4,430,760 A | 2/1984 | Smestad | |
| 4,434,797 A | 3/1984 | Silander | |
| 4,437,191 A | 3/1984 | Van der Zat et al. | |
| 4,437,362 A * | 3/1984 | Hurst | 294/65.5 |
| 4,442,655 A | 4/1984 | Stroetmann | |
| 4,444,180 A | 4/1984 | Schneider et al. | |
| 4,445,509 A | 5/1984 | Auth | |
| 4,447,227 A | 5/1984 | Kotsanis | |
| 4,448,194 A | 5/1984 | DiGiovanni et al. | |
| 4,450,591 A | 5/1984 | Rappaport | |
| 4,453,421 A | 6/1984 | Umano | |
| 4,453,539 A | 6/1984 | Raftopoulos et al. | |
| 4,456,005 A | 6/1984 | Lichty | |
| 4,457,302 A | 7/1984 | Caspari et al. | |
| 4,461,281 A | 7/1984 | Carson | |
| 4,466,429 A | 8/1984 | Loscher et al. | |
| 4,466,888 A | 8/1984 | Verkaart | |
| 4,472,840 A | 9/1984 | Jefferies | |
| 4,474,177 A | 10/1984 | Whiteside | |
| 4,484,579 A | 11/1984 | Meno et al. | |
| 4,485,096 A | 11/1984 | Bell | |
| 4,487,203 A | 12/1984 | Androphy | |
| 4,493,317 A | 1/1985 | Klaue | |
| 4,495,664 A | 1/1985 | Blanquaert | |
| 4,501,031 A | 2/1985 | McDaniel et al. | |
| 4,501,266 A | 2/1985 | McDaniel | |
| 4,501,269 A | 2/1985 | Bagby | |
| 4,502,159 A | 3/1985 | Woodroof et al. | |
| 4,502,161 A | 3/1985 | Wall | |
| 4,504,268 A | 3/1985 | Herlitze | |
| 4,505,274 A | 3/1985 | Speelman | |
| 4,506,681 A | 3/1985 | Mundell | |
| 4,509,518 A | 4/1985 | McGarry et al. | |
| 4,514,125 A | 4/1985 | Stol | |
| 4,516,276 A | 5/1985 | Mittelmeier et al. | |
| 4,526,173 A | 7/1985 | Sheehan | |
| 4,532,926 A | 8/1985 | O'Holla | |
| 4,535,757 A | 8/1985 | Webster, Jr. | |
| 4,535,772 A | 8/1985 | Sheehan | |
| 4,540,404 A | 9/1985 | Wolvek | |
| 4,541,423 A | 9/1985 | Barber | |
| 4,543,375 A | 9/1985 | Doebler et al. | |
| 4,545,374 A | 10/1985 | Jacobson | |
| 4,545,375 A | 10/1985 | Cline | |
| 4,547,327 A | 10/1985 | Bruins et al. | |
| 4,551,135 A | 11/1985 | Gorman et al. | |
| 4,553,272 A | 11/1985 | Mears | |
| 4,554,686 A | 11/1985 | Baker | |
| 4,555,242 A | 11/1985 | Saudagar | |
| 4,556,059 A | 12/1985 | Adamson, Jr. | |
| 4,556,350 A | 12/1985 | Bernhardt et al. | |
| 4,556,391 A | 12/1985 | Tardivel et al. | |
| 4,562,598 A | 1/1986 | Kranz | |
| 4,565,192 A | 1/1986 | Shapiro | |
| 4,566,138 A | 1/1986 | Lewis et al. | |
| 4,572,186 A | 2/1986 | Gould et al. | |
| 4,573,448 A | 3/1986 | Kambin | |
| 4,574,794 A | 3/1986 | Cooke et al. | |
| 4,575,371 A | 3/1986 | Nordqvist et al. | |
| 4,584,722 A | 4/1986 | Levy et al. | |
| 4,585,000 A | 4/1986 | Hershenson | |
| 4,585,282 A | 4/1986 | Bosley | |
| 4,589,414 A | 5/1986 | Yoshida et al. | |
| 4,589,686 A | 5/1986 | McGrew | |
| 4,589,868 A | 5/1986 | Dretler | |
| 4,590,928 A | 5/1986 | Hunt et al. | |
| 4,597,379 A | 7/1986 | Kihn et al. | |
| 4,599,085 A | 7/1986 | Riess et al. | |
| 4,601,893 A | 7/1986 | Cardinal | |
| 4,603,694 A | 8/1986 | Wheeler | |
| 4,606,335 A | 8/1986 | Wedeen | |
| 4,608,052 A | 8/1986 | Van Kampen et al. | |
| 4,608,965 A | 9/1986 | Anspach, Jr. et al. | |
| 4,610,662 A | 9/1986 | Weikl et al. | |
| 4,611,593 A | 9/1986 | Fogarty et al. | |
| 4,615,717 A | 10/1986 | Neubauer et al. | |
| 4,619,391 A | 10/1986 | Sharkany et al. | |
| 4,621,640 A | 11/1986 | Mulhollan et al. | |
| 4,623,553 A | 11/1986 | Ries et al. | |
| 4,624,254 A | 11/1986 | McGarry et al. | |
| 4,630,609 A | 12/1986 | Chin | |
| 4,632,101 A | 12/1986 | Freedland | |

(56) References Cited

U.S. PATENT DOCUMENTS

| | | |
|---|---|---|
| 4,641,648 A | 2/1987 | Shapiro |
| 4,642,117 A | 2/1987 | Nguyen et al. |
| 4,642,120 A | 2/1987 | Nevo et al. |
| 4,645,503 A | 2/1987 | Lin et al. |
| 4,646,736 A | 3/1987 | Auth |
| 4,646,738 A | 3/1987 | Trott |
| 4,649,918 A | 3/1987 | Pegg et al. |
| 4,651,717 A | 3/1987 | Jakubczak |
| 4,651,752 A | 3/1987 | Fuerst |
| 4,654,464 A | 3/1987 | Mittelmeier et al. |
| 4,657,460 A | 4/1987 | Bien |
| 4,657,548 A | 4/1987 | Nichols |
| 4,659,268 A | 4/1987 | Del Mundo et al. |
| 4,662,063 A | 5/1987 | Collins et al. |
| 4,662,068 A | 5/1987 | Polonsky |
| 4,662,372 A | 5/1987 | Sharkany et al. |
| 4,662,887 A | 5/1987 | Turner et al. |
| 4,669,473 A | 6/1987 | Richards et al. |
| 4,678,470 A | 7/1987 | Nashef et al. |
| 4,681,106 A | 7/1987 | Kensey et al. |
| 4,681,107 A | 7/1987 | Kees, Jr. |
| 4,682,598 A | 7/1987 | Beraha |
| 4,685,458 A | 8/1987 | Leckrone |
| 4,685,460 A | 8/1987 | Thornton |
| 4,688,998 A | 8/1987 | Olsen |
| 4,691,741 A | 9/1987 | Affa et al. |
| 4,696,667 A | 9/1987 | Masch |
| 4,705,040 A | 11/1987 | Mueller et al. |
| 4,706,659 A | 11/1987 | Matthews et al. |
| 4,706,670 A | 11/1987 | Andersen et al. |
| 4,708,139 A | 11/1987 | Dunbar, IV |
| 4,711,233 A | 12/1987 | Brown |
| 4,712,542 A | 12/1987 | Daniel et al. |
| 4,713,076 A | 12/1987 | Draenert |
| 4,713,077 A | 12/1987 | Small |
| 4,714,074 A | 12/1987 | Rey et al. |
| 4,716,893 A | 1/1988 | Fischer et al. |
| 4,716,901 A | 1/1988 | Jackson et al. |
| 4,718,909 A | 1/1988 | Brown |
| 4,718,916 A | 1/1988 | Morscher |
| 4,719,908 A | 1/1988 | Averill et al. |
| 4,721,096 A | 1/1988 | Naughton et al. |
| 4,721,103 A | 1/1988 | Freedland |
| 4,721,104 A | 1/1988 | Kaufman et al. |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A | 4/1988 | Sapega et al. |
| 4,741,330 A | 5/1988 | Hayhurst |
| 4,743,229 A | 5/1988 | Chu |
| 4,743,259 A | 5/1988 | Bolander et al. |
| 4,744,364 A | 5/1988 | Kensey |
| 4,747,405 A | 5/1988 | Leckrone |
| 4,749,585 A | 6/1988 | Greco et al. |
| 4,750,488 A | 6/1988 | Wuchinich et al. |
| 4,750,492 A | 6/1988 | Jacobs |
| 4,751,922 A | 6/1988 | DiPietropolo |
| 4,755,184 A | 7/1988 | Silverberg |
| 4,759,350 A | 7/1988 | Dunn et al. |
| 4,768,507 A | 9/1988 | Fischell |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,779,611 A | 10/1988 | Grooters et al. |
| 4,781,182 A | 11/1988 | Purnell et al. |
| 4,781,681 A | 11/1988 | Sharrow et al. |
| 4,781,922 A | 11/1988 | Bone |
| 4,784,133 A | 11/1988 | Mackin |
| 4,789,663 A | 12/1988 | Wallace et al. |
| 4,790,303 A | 12/1988 | Steffee |
| 4,790,819 A | 12/1988 | Li et al. |
| 4,792,336 A | 12/1988 | Hlavacek et al. |
| 4,793,359 A | 12/1988 | Sharrow |
| 4,794,854 A | 1/1989 | Swaim |
| 4,795,467 A | 1/1989 | Piez et al. |
| 4,796,629 A | 1/1989 | Grayzel |
| 4,798,205 A | 1/1989 | Bonomo et al. |
| 4,798,213 A | 1/1989 | Doppelt |
| 4,800,901 A | 1/1989 | Rosenberg |
| 4,801,299 A | 1/1989 | Brendel et al. |
| 4,802,479 A | 2/1989 | Haber et al. |
| 4,817,591 A | 4/1989 | Klause |
| 4,817,602 A | 4/1989 | Beraha |
| 4,822,224 A | 4/1989 | Carl et al. |
| 4,823,794 A | 4/1989 | Pierce |
| 4,825,857 A | 5/1989 | Kenna |
| 4,828,563 A | 5/1989 | Muller-Lierheim |
| 4,832,025 A | 5/1989 | Coates |
| 4,832,026 A | 5/1989 | Jones |
| 4,832,683 A | 5/1989 | Idemoto et al. |
| 4,834,752 A | 5/1989 | Van Kampen |
| 4,834,757 A | 5/1989 | Brantigan |
| 4,841,960 A | 6/1989 | Garner |
| 4,842,517 A | 6/1989 | Kawahara et al. |
| 4,843,112 A | 6/1989 | Gerhart |
| 4,844,064 A | 7/1989 | Thimsen et al. |
| 4,846,791 A | 7/1989 | Hattler et al. |
| 4,846,812 A | 7/1989 | Walker et al. |
| 4,846,835 A | 7/1989 | Grande |
| 4,857,045 A | 8/1989 | Rydell |
| 4,861,334 A | 8/1989 | Nawaz |
| 4,862,874 A | 9/1989 | Kellner |
| 4,862,882 A | 9/1989 | Venturi et al. |
| 4,862,974 A | 9/1989 | Warren et al. |
| 4,863,472 A | 9/1989 | Tormala et al. |
| 4,867,157 A | 9/1989 | McGurk-Burleson et al. |
| 4,869,242 A | 9/1989 | Galluzzo |
| 4,870,957 A | 10/1989 | Goble et al. |
| 4,875,468 A | 10/1989 | Krauter et al. |
| 4,877,020 A | 10/1989 | Vich |
| 4,880,429 A | 11/1989 | Stone |
| 4,883,048 A | 11/1989 | Purnell et al. |
| 4,883,666 A | 11/1989 | Sabel et al. |
| 4,888,022 A | 12/1989 | Huebsch |
| 4,890,612 A | 1/1990 | Kensey |
| 4,892,552 A | 1/1990 | Ainsworth et al. |
| 4,895,148 A | 1/1990 | Bays et al. |
| 4,898,156 A | 2/1990 | Gatturna et al. |
| 4,899,729 A | 2/1990 | Gill et al. |
| 4,899,743 A | 2/1990 | Nicholson et al. |
| 4,899,744 A | 2/1990 | Fujitsuka et al. |
| 4,901,721 A | 2/1990 | Hakki |
| 4,902,296 A | 2/1990 | Bolander et al. |
| 4,904,259 A | 2/1990 | Itay |
| 4,904,261 A | 2/1990 | Dove et al. |
| 4,909,789 A | 3/1990 | Taguchi et al. |
| 4,911,721 A | 3/1990 | Branemark et al. |
| 4,919,667 A | 4/1990 | Richmond |
| 4,921,478 A | 5/1990 | Solano et al. |
| 4,921,479 A | 5/1990 | Grayzel |
| 4,922,897 A | 5/1990 | Sapega et al. |
| 4,923,464 A | 5/1990 | DiPisa, Jr. |
| 4,924,865 A | 5/1990 | Bays et al. |
| 4,924,866 A | 5/1990 | Yoon |
| 4,927,412 A | 5/1990 | Menasche |
| 4,927,421 A | 5/1990 | Goble et al. |
| 4,932,956 A | 6/1990 | Reddy et al. |
| 4,932,959 A | 6/1990 | Horzewski et al. |
| 4,932,960 A | 6/1990 | Green et al. |
| 4,932,973 A | 6/1990 | Gendler |
| 4,935,023 A | 6/1990 | Whiteside et al. |
| 4,935,028 A | 6/1990 | Drews |
| 4,936,848 A | 6/1990 | Bagby |
| 4,936,852 A | 6/1990 | Kent et al. |
| 4,944,760 A | 7/1990 | Kenna |
| 4,945,625 A | 8/1990 | Winston |
| 4,945,896 A | 8/1990 | Gade |
| 4,946,468 A | 8/1990 | Li |
| 4,950,296 A | 8/1990 | McIntyre |
| 4,950,298 A | 8/1990 | Gustilo et al. |
| 4,952,213 A | 8/1990 | Bowman et al. |
| 4,954,126 A | 9/1990 | Wallsten |

(56) References Cited

U.S. PATENT DOCUMENTS

| | | |
|---|---|---|
| 4,955,910 A | 9/1990 | Bolesky |
| 4,957,498 A * | 9/1990 | Caspari et al. ............... 606/146 |
| 4,961,740 A | 10/1990 | Ray et al. |
| 4,961,741 A | 10/1990 | Hayhurst |
| 4,961,954 A | 10/1990 | Goldberg et al. |
| 4,963,151 A | 10/1990 | Ducheyne et al. |
| 4,963,489 A | 10/1990 | Naughton et al. |
| 4,964,862 A | 10/1990 | Arms |
| 4,964,865 A | 10/1990 | Burkhead et al. |
| 4,966,583 A | 10/1990 | Debbas |
| 4,968,298 A | 11/1990 | Michelson |
| 4,968,315 A | 11/1990 | Gatturna |
| 4,969,888 A | 11/1990 | Scholten et al. |
| 4,969,892 A | 11/1990 | Burton et al. |
| 4,969,895 A | 11/1990 | McLeod et al. |
| 4,979,949 A | 12/1990 | Matsen, III et al. |
| 4,979,957 A | 12/1990 | Hodorek |
| 4,983,179 A | 1/1991 | Sjostrom |
| 4,984,563 A | 1/1991 | Renaud |
| 4,984,564 A | 1/1991 | Yuen |
| 4,985,038 A | 1/1991 | Lyell |
| 4,990,161 A | 2/1991 | Kampner |
| 4,994,047 A | 2/1991 | Walker et al. |
| 4,994,067 A | 2/1991 | Summers |
| 4,994,071 A | 2/1991 | MacGregor |
| 4,995,868 A | 2/1991 | Brazier |
| 4,997,445 A | 3/1991 | Hodorek |
| 4,998,539 A | 3/1991 | Delsanti |
| 5,002,550 A | 3/1991 | Li |
| 5,002,557 A | 3/1991 | Hasson |
| 5,002,563 A | 3/1991 | Pyka et al. |
| 5,003,235 A | 3/1991 | Groom |
| 5,007,912 A | 4/1991 | Albrektsson et al. |
| 5,009,652 A | 4/1991 | Morgan et al. |
| 5,009,662 A | 4/1991 | Wallace et al. |
| 5,009,663 A | 4/1991 | Broome |
| 5,009,664 A | 4/1991 | Sievers |
| 5,013,316 A | 5/1991 | Goble et al. |
| 5,015,247 A | 5/1991 | Michelson |
| 5,015,255 A | 5/1991 | Kuslich |
| 5,019,090 A | 5/1991 | Pinchuk |
| 5,019,104 A | 5/1991 | Whiteside et al. |
| 5,021,056 A | 6/1991 | Hofmann et al. |
| 5,021,059 A | 6/1991 | Kensey et al. |
| 5,026,373 A | 6/1991 | Ray et al. |
| 5,032,132 A | 7/1991 | Matsen, III et al. |
| 5,035,699 A | 7/1991 | Coates |
| 5,035,713 A | 7/1991 | Friis |
| 5,037,404 A | 8/1991 | Gold et al. |
| 5,037,422 A | 8/1991 | Hayhurst et al. |
| 5,037,423 A | 8/1991 | Kenna |
| 5,041,093 A | 8/1991 | Chu |
| 5,041,114 A | 8/1991 | Chapman et al. |
| 5,041,125 A | 8/1991 | Montano, Jr. |
| 5,041,129 A | 8/1991 | Hayhurst et al. |
| 5,042,976 A | 8/1991 | Ishitsu et al. |
| 5,046,513 A | 9/1991 | Gatturna et al. |
| 5,047,055 A | 9/1991 | Bao et al. |
| 5,051,049 A | 9/1991 | Wills |
| 5,053,009 A | 10/1991 | Herzberg |
| 5,053,039 A | 10/1991 | Hofmann et al. |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,060,678 A | 10/1991 | Bauman et al. |
| 5,061,274 A | 10/1991 | Kensey |
| 5,061,281 A | 10/1991 | Mares et al. |
| 5,061,286 A | 10/1991 | Lyle |
| 5,062,843 A | 11/1991 | Mahony, III |
| 5,069,674 A | 12/1991 | Fearnot et al. |
| 5,071,411 A | 12/1991 | Hillstead |
| 5,073,373 A | 12/1991 | O'Leary et al. |
| 5,078,731 A | 1/1992 | Hayhurst |
| 5,078,744 A | 1/1992 | Chvapil |
| 5,078,745 A | 1/1992 | Rhenter et al. |
| 5,082,670 A | 1/1992 | Gage et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,092,348 A | 3/1992 | Dubrul et al. |
| 5,098,433 A | 3/1992 | Freedland |
| 5,098,434 A | 3/1992 | Serbousek |
| 5,098,436 A | 3/1992 | Ferrante et al. |
| 5,098,437 A | 3/1992 | Kashuba et al. |
| 5,099,859 A | 3/1992 | Bell |
| 5,100,405 A | 3/1992 | McLaren |
| 5,100,409 A | 3/1992 | Coates et al. |
| 5,100,417 A | 3/1992 | Cerier et al. |
| 5,100,689 A | 3/1992 | Goldberg et al. |
| 5,101,720 A | 4/1992 | Bianchi |
| 5,102,417 A | 4/1992 | Palmaz |
| 5,102,421 A | 4/1992 | Anspach, Jr. |
| 5,104,383 A | 4/1992 | Shichman |
| 5,108,399 A | 4/1992 | Eitenmuller et al. |
| 5,108,433 A | 4/1992 | May et al. |
| 5,108,441 A | 4/1992 | McDowell |
| 5,111,987 A | 5/1992 | Moeinzadeh et al. |
| 5,116,374 A | 5/1992 | Stone |
| 5,120,175 A | 6/1992 | Arbegast et al. |
| 5,122,122 A | 6/1992 | Allgood |
| 5,122,144 A | 6/1992 | Bert et al. |
| 5,123,520 A | 6/1992 | Schmid et al. |
| 5,123,906 A | 6/1992 | Kelman |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller |
| 5,139,520 A | 8/1992 | Rosenberg |
| 5,141,520 A | 8/1992 | Goble et al. |
| 5,143,062 A | 9/1992 | Peckham |
| 5,143,093 A | 9/1992 | Sahota |
| 5,147,362 A | 9/1992 | Goble |
| 5,152,744 A | 10/1992 | Krause et al. |
| 5,152,765 A | 10/1992 | Ross et al. |
| 5,152,778 A | 10/1992 | Bales, Jr. et al. |
| 5,154,717 A | 10/1992 | Matsen, III et al. |
| 5,154,720 A | 10/1992 | Trott et al. |
| 5,156,613 A | 10/1992 | Sawyer |
| 5,156,616 A | 10/1992 | Meadows et al. |
| 5,158,553 A | 10/1992 | Berry et al. |
| 5,158,566 A | 10/1992 | Pianetti |
| 5,158,571 A | 10/1992 | Picha |
| 5,158,934 A | 10/1992 | Ammann et al. |
| 5,159,921 A | 11/1992 | Hoover |
| 5,162,506 A | 11/1992 | Hadden |
| 5,163,949 A | 11/1992 | Bonutti |
| 5,163,960 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,251 A | 12/1992 | Bregen et al. |
| 5,171,276 A | 12/1992 | Caspari et al. |
| 5,174,300 A | 12/1992 | Bales et al. |
| 5,176,682 A | 1/1993 | Chow |
| 5,176,684 A | 1/1993 | Ferrante et al. |
| 5,176,702 A | 1/1993 | Bales et al. |
| 5,178,622 A | 1/1993 | Lehner, II |
| 5,179,964 A | 1/1993 | Cook |
| 5,180,388 A | 1/1993 | DiCarlo |
| 5,183,053 A | 2/1993 | Yeh et al. |
| 5,183,464 A | 2/1993 | Dubrul et al. |
| 5,186,178 A | 2/1993 | Yeh et al. |
| 5,192,287 A | 3/1993 | Fournier et al. |
| 5,192,326 A | 3/1993 | Bao et al. |
| 5,192,327 A | 3/1993 | Brantigan |
| 5,195,507 A | 3/1993 | Bilweis |
| 5,195,970 A | 3/1993 | Gahara |
| 5,197,166 A | 3/1993 | Meier et al. |
| 5,197,488 A | 3/1993 | Kovacevic |
| 5,197,955 A | 3/1993 | Stephens et al. |
| 5,197,968 A | 3/1993 | Clement |
| 5,197,971 A | 3/1993 | Bonutti |

(56) References Cited

U.S. PATENT DOCUMENTS

| | | |
|---|---|---|
| 5,197,987 A | 3/1993 | Koch et al. |
| 5,201,768 A | 4/1993 | Caspari et al. |
| 5,203,784 A | 4/1993 | Ross et al. |
| 5,203,787 A | 4/1993 | Noblitt |
| 5,204,106 A | 4/1993 | Schepers et al. |
| 5,207,692 A | 5/1993 | Kraus et al. |
| 5,208,950 A | 5/1993 | Merritt |
| 5,209,776 A | 5/1993 | Bass et al. |
| 5,211,647 A | 5/1993 | Schmieding |
| 5,217,463 A | 6/1993 | Mikhail |
| 5,217,486 A | 6/1993 | Rice et al. |
| 5,217,493 A | 6/1993 | Raad et al. |
| 5,219,359 A | 6/1993 | McQuilkin et al. |
| 5,224,946 A | 7/1993 | Hayhurst et al. |
| 5,226,426 A | 7/1993 | Yoon |
| 5,226,899 A | 7/1993 | Lee et al. |
| 5,226,915 A | 7/1993 | Bertin |
| 5,228,459 A | 7/1993 | Caspari et al. |
| 5,234,006 A | 8/1993 | Eaton et al. |
| 5,234,425 A | 8/1993 | Fogarty et al. |
| 5,234,433 A | 8/1993 | Bert et al. |
| 5,236,432 A | 8/1993 | Matsen, III et al. |
| 5,236,438 A | 8/1993 | Wilk |
| 5,236,445 A | 8/1993 | Hayhurst et al. |
| 5,242,902 A | 9/1993 | Murphy et al. |
| 5,244,946 A | 9/1993 | Guest et al. |
| 5,246,441 A | 9/1993 | Ross et al. |
| 5,250,026 A | 10/1993 | Ehrlich et al. |
| 5,250,055 A | 10/1993 | Moore et al. |
| 5,250,070 A | 10/1993 | Parodi |
| 5,254,091 A | 10/1993 | Aliahmad et al. |
| 5,254,113 A | 10/1993 | Wilk |
| 5,258,004 A | 11/1993 | Bales et al. |
| 5,258,007 A | 11/1993 | Spetzler et al. |
| 5,258,015 A | 11/1993 | Li et al. |
| 5,258,016 A | 11/1993 | DiPoto et al. |
| 5,258,031 A | 11/1993 | Salib et al. |
| 5,258,032 A | 11/1993 | Bertin |
| 5,261,914 A | 11/1993 | Warren |
| 5,263,498 A | 11/1993 | Caspari et al. |
| 5,263,987 A | 11/1993 | Shah |
| 5,266,325 A | 11/1993 | Kuzma et al. |
| 5,269,783 A | 12/1993 | Sander |
| 5,269,785 A | 12/1993 | Bonutti |
| 5,269,809 A | 12/1993 | Hayhurst et al. |
| 5,273,524 A | 12/1993 | Fox et al. |
| 5,275,166 A | 1/1994 | Vaitekunas et al. |
| 5,281,235 A | 1/1994 | Haber et al. |
| 5,282,803 A | 2/1994 | Lackey |
| 5,282,832 A | 2/1994 | Toso et al. |
| 5,282,861 A | 2/1994 | Kaplan |
| 5,284,655 A | 2/1994 | Bogdansky et al. |
| 5,285,655 A | 2/1994 | Sung-Il et al. |
| 5,290,249 A | 3/1994 | Foster et al. |
| 5,290,281 A | 3/1994 | Tschakaloff |
| 5,298,254 A | 3/1994 | Prewett et al. |
| 5,304,119 A | 4/1994 | Balaban et al. |
| 5,304,181 A | 4/1994 | Caspari et al. |
| 5,306,280 A | 4/1994 | Bregen et al. |
| 5,306,301 A | 4/1994 | Graf et al. |
| 5,312,438 A | 5/1994 | Johnson |
| 5,315,741 A | 5/1994 | Dubberke |
| 5,318,588 A | 6/1994 | Horzewski et al. |
| 5,320,611 A | 6/1994 | Bonutti |
| 5,322,505 A | 6/1994 | Krause et al. |
| 5,324,308 A | 6/1994 | Pierce |
| 5,326,361 A | 7/1994 | Hollister |
| 5,328,480 A | 7/1994 | Melker et al. |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot et al. |
| 5,330,486 A | 7/1994 | Wilk |
| 5,330,497 A | 7/1994 | Freitas et al. |
| 5,331,975 A | 7/1994 | Bonutti |
| 5,334,146 A | 8/1994 | Ozasa |
| 5,334,965 A | 8/1994 | Dolgin |
| 5,336,231 A | 8/1994 | Adair |
| 5,336,240 A | 8/1994 | Metzler et al. |
| 5,339,799 A | 8/1994 | Kami et al. |
| 5,345,927 A | 9/1994 | Bonutti |
| 5,349,956 A | 9/1994 | Bonutti |
| 5,352,229 A | 10/1994 | Goble et al. |
| 5,354,298 A | 10/1994 | Lee et al. |
| 5,354,302 A | 10/1994 | Ko |
| 5,356,413 A | 10/1994 | Martins et al. |
| 5,360,450 A | 11/1994 | Giannini |
| 5,366,480 A | 11/1994 | Corriveau et al. |
| 5,370,646 A | 12/1994 | Reese et al. |
| 5,370,660 A | 12/1994 | Weinstein et al. |
| 5,370,662 A | 12/1994 | Stone et al. |
| 5,372,146 A | 12/1994 | Branch |
| 5,374,235 A | 12/1994 | Ahrens |
| 5,376,101 A | 12/1994 | Green et al. |
| 5,376,126 A | 12/1994 | Lin |
| 5,379,759 A | 1/1995 | Sewell, Jr. |
| 5,382,254 A | 1/1995 | McGarry et al. |
| 5,383,883 A | 1/1995 | Wilk et al. |
| 5,383,905 A | 1/1995 | Golds et al. |
| 5,383,937 A | 1/1995 | Mikhail |
| RE34,866 E | 2/1995 | Kensey et al. |
| 5,390,683 A | 2/1995 | Pisharodi |
| 5,391,171 A | 2/1995 | Schmieding |
| 5,391,173 A | 2/1995 | Wilk |
| RE34,871 E | 3/1995 | McGuire et al. |
| 5,395,033 A | 3/1995 | Byrne |
| 5,395,308 A | 3/1995 | Fox et al. |
| 5,395,376 A | 3/1995 | Caspari et al. |
| 5,397,311 A | 3/1995 | Walker et al. |
| 5,400,805 A | 3/1995 | Warren |
| 5,403,312 A | 4/1995 | Yates et al. |
| 5,403,317 A | 4/1995 | Bonutti |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,415,663 A | 5/1995 | Luckman et al. |
| 5,417,691 A | 5/1995 | Hayhurst |
| 5,417,700 A | 5/1995 | Egan |
| 5,417,701 A * | 5/1995 | Holmes .................. 606/148 |
| 5,417,712 A | 5/1995 | Whittaker et al. |
| 5,423,796 A | 6/1995 | Shikhman et al. |
| 5,423,819 A | 6/1995 | Small et al. |
| 5,423,860 A | 6/1995 | Lizardi et al. |
| 5,425,733 A | 6/1995 | Schmieding |
| 5,431,670 A * | 7/1995 | Holmes .................. 606/147 |
| 5,439,470 A | 8/1995 | Li |
| 5,441,502 A | 8/1995 | Bartlett |
| 5,441,538 A | 8/1995 | Bonutti |
| 5,443,482 A | 8/1995 | Stone et al. |
| 5,443,512 A | 8/1995 | Parr et al. |
| 5,445,615 A | 8/1995 | Yoon |
| 5,447,503 A | 9/1995 | Miller |
| 5,449,372 A | 9/1995 | Schmaltz et al. |
| 5,449,382 A | 9/1995 | Dayton |
| 5,451,235 A | 9/1995 | Lock |
| 5,453,090 A | 9/1995 | Martinez et al. |
| 5,454,365 A | 10/1995 | Bonutti |
| 5,456,722 A | 10/1995 | McLeod et al. |
| 5,458,653 A | 10/1995 | Davidson |
| 5,462,549 A | 10/1995 | Glock |
| 5,462,561 A | 10/1995 | Voda |
| 5,464,424 A | 11/1995 | O'Donnell, Jr. |
| 5,464,425 A | 11/1995 | Skiba |
| 5,464,426 A | 11/1995 | Bonutti |
| 5,464,427 A | 11/1995 | Curtis et al. |
| 5,470,337 A | 11/1995 | Moss |
| 5,472,444 A | 12/1995 | Huebner et al. |
| 5,474,554 A | 12/1995 | Ku |
| 5,474,559 A | 12/1995 | Bertin et al. |
| 5,478,351 A | 12/1995 | Meade et al. |
| 5,478,353 A | 12/1995 | Yoon |
| 5,480,403 A | 1/1996 | Lee et al. |
| 5,484,437 A | 1/1996 | Michelson |

(56) References Cited

U.S. PATENT DOCUMENTS

| | | |
|---|---|---|
| 5,486,197 A | 1/1996 | Le et al. |
| 5,487,844 A | 1/1996 | Fujita |
| 5,488,958 A | 2/1996 | Topel et al. |
| 5,492,697 A | 2/1996 | Boyan et al. |
| 5,496,292 A | 3/1996 | Burnham |
| 5,496,335 A | 3/1996 | Thomason et al. |
| 5,496,348 A | 3/1996 | Bonutti |
| 5,500,000 A | 3/1996 | Feagin et al. |
| 5,501,700 A | 3/1996 | Hirata |
| 5,504,977 A | 4/1996 | Weppner |
| 5,505,735 A | 4/1996 | Li |
| 5,507,754 A | 4/1996 | Green et al. |
| 5,514,091 A | 5/1996 | Yoon |
| 5,514,153 A | 5/1996 | Bonutti |
| 5,520,700 A | 5/1996 | Beyar et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |
| 5,540,718 A | 7/1996 | Bartlett |
| 5,542,423 A | 8/1996 | Bonutti |
| 5,542,947 A | 8/1996 | Treacy |
| 5,545,178 A | 8/1996 | Kensey et al. |
| 5,545,180 A | 8/1996 | Le et al. |
| 5,545,206 A | 8/1996 | Carson |
| 5,545,222 A | 8/1996 | Bonutti |
| 5,549,630 A | 8/1996 | Bonutti |
| 5,549,631 A | 8/1996 | Bonutti |
| 5,549,689 A | 8/1996 | Epstein et al. |
| 5,550,172 A | 8/1996 | Regula et al. |
| 5,556,402 A | 9/1996 | Xu |
| 5,562,668 A | 10/1996 | Johnson |
| 5,562,684 A | 10/1996 | Kammerer |
| 5,562,688 A | 10/1996 | Riza |
| 5,569,252 A | 10/1996 | Justin et al. |
| 5,569,259 A | 10/1996 | Ferrante et al. |
| 5,569,305 A | 10/1996 | Bonutti |
| 5,569,306 A | 10/1996 | Thal |
| 5,571,139 A | 11/1996 | Jenkins, Jr. |
| 5,571,196 A | 11/1996 | Stein |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer et al. |
| 5,577,517 A | 11/1996 | Bonutti |
| 5,580,344 A | 12/1996 | Hasson |
| 5,584,835 A | 12/1996 | Greenfield |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van De Moer et al. |
| 5,593,425 A | 1/1997 | Bonutti et al. |
| 5,593,625 A | 1/1997 | Riebel et al. |
| 5,595,563 A | 1/1997 | Moisdon |
| 5,601,557 A | 2/1997 | Hayhurst |
| 5,601,558 A | 2/1997 | Torrie et al. |
| 5,601,565 A | 2/1997 | Huebner |
| 5,607,427 A | 3/1997 | Tschakaloff |
| 5,609,595 A | 3/1997 | Pennig |
| 5,609,635 A | 3/1997 | Michelson |
| 5,618,314 A | 4/1997 | Harwin et al. |
| 5,620,448 A | 4/1997 | Puddu |
| 5,620,461 A | 4/1997 | Muijs Van De Moer et al. |
| 5,624,462 A | 4/1997 | Bonutti |
| 5,624,463 A | 4/1997 | Stone et al. |
| 5,626,612 A | 5/1997 | Bartlett |
| 5,626,614 A | 5/1997 | Hart |
| 5,626,718 A | 5/1997 | Philippe et al. |
| 5,628,751 A | 5/1997 | Sander et al. |
| 5,630,824 A | 5/1997 | Hart |
| 5,631,617 A | 5/1997 | Morishita |
| 5,634,926 A | 6/1997 | Jobe |
| 5,643,274 A | 7/1997 | Sander et al. |
| 5,643,293 A | 7/1997 | Kogasaka et al. |
| 5,643,295 A | 7/1997 | Yoon |
| 5,643,320 A | 7/1997 | Lower et al. |
| 5,643,321 A | 7/1997 | McDevitt |
| 5,644,002 A | 7/1997 | Cooper et al. |
| 5,645,553 A | 7/1997 | Kolesa et al. |
| 5,645,588 A | 7/1997 | Graf et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,662,710 A | 9/1997 | Bonutti |
| 5,665,089 A | 9/1997 | Dall et al. |
| 5,665,109 A | 9/1997 | Yoon |
| 5,665,112 A | 9/1997 | Thal |
| 5,667,513 A | 9/1997 | Torrie et al. |
| 5,667,520 A | 9/1997 | Bonutti |
| 5,669,909 A | 9/1997 | Zdeblick et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,682,886 A | 11/1997 | Delp et al. |
| 5,683,401 A | 11/1997 | Schmieding et al. |
| 5,683,418 A | 11/1997 | Luscombe et al. |
| 5,683,469 A | 11/1997 | Johnson et al. |
| 5,685,820 A | 11/1997 | Riek et al. |
| 5,685,826 A | 11/1997 | Bonutti |
| 5,688,283 A | 11/1997 | Knapp |
| 5,690,654 A | 11/1997 | Ovil |
| 5,690,655 A | 11/1997 | Hart et al. |
| 5,690,674 A | 11/1997 | Diaz |
| 5,690,676 A | 11/1997 | DiPoto et al. |
| 5,693,055 A | 12/1997 | Zahiri et al. |
| 5,694,951 A | 12/1997 | Bonutti |
| 5,697,950 A | 12/1997 | Fucci et al. |
| 5,702,397 A | 12/1997 | Gonle et al. |
| 5,702,462 A | 12/1997 | Oberlander |
| 5,707,390 A | 1/1998 | Bonutti |
| 5,707,395 A | 1/1998 | Li |
| 5,713,897 A | 2/1998 | Goble et al. |
| 5,713,903 A | 2/1998 | Sander et al. |
| 5,713,921 A | 2/1998 | Bonutti |
| 5,715,836 A | 2/1998 | Kliegis et al. |
| 5,716,325 A | 2/1998 | Bonutti |
| 5,718,717 A | 2/1998 | Bonutti |
| 5,720,747 A | 2/1998 | Burke |
| 5,720,753 A | 2/1998 | Sander et al. |
| 5,722,978 A | 3/1998 | Jenkins, Jr. |
| 5,723,016 A | 3/1998 | Minns et al. |
| 5,725,529 A | 3/1998 | Nicholson et al. |
| 5,725,541 A | 3/1998 | Anspach, III et al. |
| 5,725,556 A | 3/1998 | Moser et al. |
| 5,725,557 A | 3/1998 | Gatturna et al. |
| 5,725,582 A | 3/1998 | Bevan |
| 5,730,747 A * | 3/1998 | Ek et al. ............ 606/148 |
| 5,733,306 A | 3/1998 | Bonutti |
| 5,735,875 A | 4/1998 | Bonutti et al. |
| 5,735,877 A | 4/1998 | Pagedas |
| 5,735,899 A | 4/1998 | Schwartz et al. |
| 5,741,268 A | 4/1998 | Schutz |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,763,416 A | 6/1998 | Bonadio et al. |
| 5,766,221 A | 6/1998 | Benderev et al. |
| 5,766,251 A | 6/1998 | Koshino |

(56) References Cited

U.S. PATENT DOCUMENTS

| | | |
|---|---|---|
| 5,769,854 A | 6/1998 | Bastian et al. |
| 5,769,894 A | 6/1998 | Ferragamo |
| 5,772,672 A | 6/1998 | Toy et al. |
| 5,776,151 A | 7/1998 | Chan |
| 5,779,706 A | 7/1998 | Tschakaloff |
| 5,779,719 A | 7/1998 | Klein et al. |
| 5,779,728 A | 7/1998 | Lunsford et al. |
| 5,782,862 A | 7/1998 | Bonutti |
| 5,782,925 A | 7/1998 | Collazo et al. |
| 5,785,713 A | 7/1998 | Jobe |
| 5,792,096 A | 8/1998 | Rentmeester et al. |
| 5,797,931 A | 8/1998 | Bito et al. |
| 5,797,963 A | 8/1998 | McDevitt |
| 5,800,537 A | 9/1998 | Bell |
| 5,800,544 A | 9/1998 | Demopulos et al. |
| 5,806,518 A | 9/1998 | Mittelstadt |
| 5,807,403 A | 9/1998 | Beyar et al. |
| 5,810,827 A | 9/1998 | Haines et al. |
| 5,810,849 A | 9/1998 | Kontos |
| 5,810,853 A | 9/1998 | Yoon |
| 5,810,884 A | 9/1998 | Kim |
| 5,814,071 A | 9/1998 | McDevitt et al. |
| 5,814,072 A | 9/1998 | Bonutti |
| 5,814,073 A | 9/1998 | Bonutti |
| 5,817,107 A | 10/1998 | Schaller |
| 5,823,938 A * | 10/1998 | Hernandez ............... 600/15 |
| 5,823,994 A | 10/1998 | Sharkey et al. |
| 5,824,009 A * | 10/1998 | Fukuda et al. ........... 606/144 |
| 5,827,269 A * | 10/1998 | Saadat ............... A61B 18/00 606/28 |
| 5,827,318 A | 10/1998 | Bonutti |
| 5,830,125 A | 11/1998 | Scribner et al. |
| 5,836,897 A | 11/1998 | Sakural et al. |
| 5,836,948 A | 11/1998 | Zucherman et al. |
| 5,839,899 A | 11/1998 | Robinson |
| 5,843,178 A | 12/1998 | Vanney et al. |
| 5,845,645 A | 12/1998 | Bonutti |
| 5,851,185 A * | 12/1998 | Berns .................. 600/434 |
| 5,860,997 A | 1/1999 | Bonutti |
| 5,865,834 A | 2/1999 | McGuire |
| 5,866,634 A | 2/1999 | Tokushige et al. |
| 5,868,749 A | 2/1999 | Reed |
| 5,871,018 A | 2/1999 | Delp et al. |
| 5,873,891 A | 2/1999 | Sohn |
| 5,874,235 A | 2/1999 | Chan |
| 5,879,372 A | 3/1999 | Bartlett |
| 5,888,196 A | 3/1999 | Bonutti |
| 5,888,219 A | 3/1999 | Bonutti |
| 5,891,166 A | 4/1999 | Schervinsky |
| 5,891,168 A | 4/1999 | Thal |
| 5,893,880 A | 4/1999 | Egan et al. |
| 5,895,426 A | 4/1999 | Scarborough et al. |
| 5,897,559 A | 4/1999 | Masini |
| 5,897,574 A | 4/1999 | Bonutti |
| 5,899,911 A | 5/1999 | Carter |
| 5,899,921 A | 5/1999 | Caspari et al. |
| 5,902,321 A | 5/1999 | Caspari et al. |
| 5,906,579 A | 5/1999 | Vander Salm et al. |
| 5,906,616 A | 5/1999 | Pavlov et al. |
| 5,906,625 A | 5/1999 | Bito et al. |
| 5,908,429 A | 6/1999 | Yoon |
| 5,911,721 A | 6/1999 | Nicholson et al. |
| 5,916,221 A | 6/1999 | Hodorek et al. |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund et al. |
| 5,921,986 A | 7/1999 | Bonutti |
| 5,925,064 A * | 7/1999 | Meyers et al. ........... 606/205 |
| 5,928,244 A | 7/1999 | Tovey et al. |
| 5,928,267 A | 7/1999 | Bonutti et al. |
| 5,931,838 A | 8/1999 | Vito |
| 5,931,869 A | 8/1999 | Boucher et al. |
| 5,935,094 A | 8/1999 | Zupkas |
| 5,935,131 A | 8/1999 | Bonutti |
| 5,940,942 A | 8/1999 | Fong |
| 5,941,900 A | 8/1999 | Bonutti |
| 5,941,901 A | 8/1999 | Egan |
| 5,947,982 A | 9/1999 | Duran |
| 5,948,000 A | 9/1999 | Larsen et al. |
| 5,948,001 A | 9/1999 | Larsen |
| 5,948,002 A | 9/1999 | Bonutti |
| 5,951,590 A | 9/1999 | Goldfarb |
| 5,954,739 A | 9/1999 | Bonutti |
| 5,957,953 A | 9/1999 | DiPoto et al. |
| 5,961,499 A | 10/1999 | Bonutti |
| 5,961,521 A | 10/1999 | Roger |
| 5,961,538 A | 10/1999 | Pedlick et al. |
| 5,961,554 A | 10/1999 | Janson et al. |
| 5,964,765 A | 10/1999 | Fenton, Jr. et al. |
| 5,964,769 A | 10/1999 | Wagner et al. |
| 5,968,044 A | 10/1999 | Nicholson et al. |
| 5,968,046 A | 10/1999 | Castleman |
| 5,968,047 A | 10/1999 | Reed |
| 5,980,520 A | 11/1999 | Vancaillie |
| 5,980,558 A | 11/1999 | Wiley |
| 5,980,559 A | 11/1999 | Bonutti |
| 5,984,929 A | 11/1999 | Bashiri et al. |
| 5,984,967 A | 11/1999 | Zdeblick et al. |
| 5,989,282 A | 11/1999 | Bonutti |
| 5,989,289 A | 11/1999 | Coates et al. |
| 5,993,458 A | 11/1999 | Vaitekunas et al. |
| 5,993,477 A | 11/1999 | Vaitekunas et al. |
| 6,007,537 A | 12/1999 | Burkinshaw et al. |
| 6,007,567 A | 12/1999 | Bonutti |
| 6,007,580 A | 12/1999 | Lehto et al. |
| 6,008,433 A | 12/1999 | Stone |
| 6,010,525 A | 1/2000 | Bonutti |
| 6,010,526 A | 1/2000 | Sandstrom et al. |
| 6,013,853 A | 1/2000 | Athanasiou et al. |
| 6,017,305 A | 1/2000 | Bonutti |
| 6,017,321 A | 1/2000 | Boone |
| 6,024,746 A | 2/2000 | Katz |
| 6,033,410 A | 3/2000 | McLean et al. |
| 6,033,429 A | 3/2000 | Magovern |
| 6,033,430 A | 3/2000 | Bonutti |
| 6,042,596 A | 3/2000 | Bonutti |
| 6,045,551 A | 4/2000 | Bonutti |
| 6,050,998 A | 4/2000 | Fletcher et al. |
| 6,056,751 A | 5/2000 | Fenton, Jr. |
| 6,056,754 A | 5/2000 | Haines et al. |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti et al. |
| 6,059,827 A | 5/2000 | Fenton |
| 6,059,831 A | 5/2000 | Braslow et al. |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,066,175 A | 5/2000 | Henderson et al. |
| 6,068,637 A | 5/2000 | Popov et al. |
| 6,068,648 A | 5/2000 | Cole et al. |
| 6,074,409 A | 6/2000 | Goldfarb |
| 6,077,277 A | 6/2000 | Mollenauer et al. |
| 6,077,292 A | 6/2000 | Bonutti |
| 6,080,161 A | 6/2000 | Eaves, III et al. |
| 6,083,244 A | 7/2000 | Lubbers et al. |
| 6,083,522 A | 7/2000 | Chu et al. |
| 6,086,593 A | 7/2000 | Bonutti |
| 6,086,608 A | 7/2000 | Ek et al. |
| 6,090,072 A | 7/2000 | Kratoska et al. |
| 6,099,531 A | 8/2000 | Bonutti |
| 6,099,537 A | 8/2000 | Sugai et al. |
| 6,099,547 A | 8/2000 | Gellman et al. |
| 6,099,550 A | 8/2000 | Yoon |
| 6,099,552 A | 8/2000 | Adams |
| 6,102,850 A | 8/2000 | Wang et al. |
| 6,102,928 A | 8/2000 | Bonutti |
| 6,102,950 A | 8/2000 | Vaccaro |
| 6,102,955 A | 8/2000 | Mendes et al. |
| 6,106,529 A | 8/2000 | Techiera |

(56) References Cited

U.S. PATENT DOCUMENTS

| | | |
|---|---|---|
| 6,106,545 A | 8/2000 | Egan |
| 6,110,188 A | 8/2000 | Narciso, Jr. |
| 6,110,207 A | 8/2000 | Eichhorn et al. |
| 6,117,160 A | 9/2000 | Bonutti |
| 6,120,536 A | 9/2000 | Ding et al. |
| 6,123,710 A | 9/2000 | Pinczewski et al. |
| 6,125,574 A | 10/2000 | Ganaja et al. |
| 6,126,677 A | 10/2000 | Ganaja et al. |
| 6,127,757 A | 10/2000 | Swinbanks |
| 6,132,468 A | 10/2000 | Mansmann |
| 6,132,472 A | 10/2000 | Bonutti |
| 6,139,320 A | 10/2000 | Hahn |
| RE36,974 E | 11/2000 | Bonutti |
| 6,146,385 A | 11/2000 | Torrie et al. |
| 6,149,669 A | 11/2000 | Li |
| 6,152,949 A | 11/2000 | Bonutti |
| 6,154,353 A | 11/2000 | Bowers |
| 6,155,756 A | 12/2000 | Mericle et al. |
| 6,156,070 A | 12/2000 | Incavo et al. |
| 6,159,224 A | 12/2000 | Yoon |
| 6,159,234 A | 12/2000 | Bonutti et al. |
| 6,171,236 B1 | 1/2001 | Bonutti |
| 6,171,299 B1 | 1/2001 | Bonutti |
| 6,171,307 B1 | 1/2001 | Orlich |
| 6,171,340 B1 | 1/2001 | McDowell |
| 6,174,313 B1 | 1/2001 | Bonutti |
| 6,174,314 B1 | 1/2001 | Waddell |
| 6,174,324 B1 | 1/2001 | Egan et al. |
| 6,179,840 B1 | 1/2001 | Bowman |
| 6,179,850 B1 * | 1/2001 | Goradia ............ 606/158 |
| 6,187,008 B1 | 2/2001 | Hamman |
| 6,187,023 B1 | 2/2001 | Bonutti |
| 6,190,400 B1 | 2/2001 | Van De Moer et al. |
| 6,190,401 B1 | 2/2001 | Green |
| 6,193,754 B1 | 2/2001 | Seedhom |
| 6,200,322 B1 | 3/2001 | Branch et al. |
| 6,200,329 B1 | 3/2001 | Fung et al. |
| 6,203,565 B1 | 3/2001 | Bonutti et al. |
| 6,210,317 B1 | 4/2001 | Bonlie |
| 6,214,051 B1 | 4/2001 | Badorf et al. |
| 6,217,591 B1 | 4/2001 | Egan et al. |
| 6,217,617 B1 | 4/2001 | Bonutti |
| 6,224,593 B1 | 5/2001 | Ryan |
| 6,224,630 B1 | 5/2001 | Bao et al. |
| 6,228,086 B1 | 5/2001 | Wahl et al. |
| 6,231,592 B1 | 5/2001 | Bonutti et al. |
| 6,235,057 B1 | 5/2001 | Roger et al. |
| 6,238,395 B1 | 5/2001 | Bonutti |
| 6,238,396 B1 | 5/2001 | Lombardo |
| 6,241,749 B1 | 6/2001 | Rayhanabad |
| 6,241,771 B1 | 6/2001 | Gresser et al. |
| 6,258,091 B1 | 7/2001 | Sevrain et al. |
| 6,264,675 B1 | 7/2001 | Brotz |
| 6,267,761 B1 | 7/2001 | Ryan |
| 6,273,717 B1 | 8/2001 | Hahn et al. |
| 6,277,136 B1 | 8/2001 | Bonutti |
| 6,280,474 B1 | 8/2001 | Cassidy et al. |
| 6,286,746 B1 | 9/2001 | Egan et al. |
| 6,287,325 B1 | 9/2001 | Bonutti |
| 6,293,961 B2 | 9/2001 | Schwartz et al. |
| 6,296,646 B1 | 10/2001 | Williamson |
| 6,306,159 B1 | 10/2001 | Schwartz et al. |
| 6,309,405 B1 | 10/2001 | Bonutti |
| 6,312,448 B1 | 11/2001 | Bonutti |
| 6,319,252 B1 | 11/2001 | McDevitt et al. |
| 6,319,271 B1 | 11/2001 | Schwartz et al. |
| 6,338,730 B1 | 1/2002 | Bonutti |
| 6,340,365 B2 | 1/2002 | Dittrich et al. |
| 6,342,075 B1 | 1/2002 | MacArthur |
| 6,348,056 B1 | 2/2002 | Bates et al. |
| 6,355,166 B1 * | 3/2002 | Amarasinghe ......... B01D 49/00 204/280 |
| 6,358,196 B1 | 3/2002 | Rayman |
| 6,358,266 B1 | 3/2002 | Bonutti |
| 6,358,271 B1 | 3/2002 | Egan et al. |
| 6,361,565 B1 | 3/2002 | Bonutti |
| 6,364,897 B1 | 4/2002 | Bonutti |
| 6,368,325 B1 | 4/2002 | McKinley et al. |
| 6,368,326 B1 | 4/2002 | Dakin et al. |
| 6,368,343 B1 | 4/2002 | Bonutti et al. |
| 6,371,957 B1 | 4/2002 | Amrein et al. |
| 6,373,676 B1 | 4/2002 | Baker |
| 6,387,096 B1 | 5/2002 | Hyde |
| 6,409,742 B1 | 6/2002 | Fulton, III |
| 6,409,743 B1 | 6/2002 | Fenton, Jr. |
| 6,419,704 B1 | 7/2002 | Ferree |
| 6,423,063 B1 | 7/2002 | Bonutti |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer et al. |
| 6,447,516 B1 | 9/2002 | Bonutti |
| 6,450,985 B1 | 9/2002 | Schoelling et al. |
| 6,451,042 B1 | 9/2002 | Bonutti |
| 6,461,360 B1 | 10/2002 | Adams |
| 6,464,713 B2 | 10/2002 | Bonutti |
| 6,468,289 B1 | 10/2002 | Bonutti |
| 6,468,293 B2 | 10/2002 | Bonutti |
| 6,471,715 B1 | 10/2002 | Weiss |
| 6,471,724 B2 | 10/2002 | Zdeblick et al. |
| 6,475,230 B1 | 11/2002 | Bonutti |
| 6,482,209 B1 | 11/2002 | Engh et al. |
| 6,488,196 B1 | 12/2002 | Fenton |
| 6,500,179 B1 | 12/2002 | Masini |
| 6,500,195 B2 | 12/2002 | Bonutti |
| 6,503,259 B2 | 1/2003 | Huxel et al. |
| 6,503,267 B2 | 1/2003 | Bonutti et al. |
| 6,503,277 B2 | 1/2003 | Bonutti |
| 6,527,774 B2 | 3/2003 | Lieberman |
| 6,530,933 B1 | 3/2003 | Yeung et al. |
| 6,535,764 B2 | 3/2003 | Imran et al. |
| 6,540,786 B2 | 4/2003 | Chibrac et al. |
| 6,543,455 B2 | 4/2003 | Bonutti |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,554,852 B1 | 4/2003 | Oberlander |
| 6,557,426 B2 | 5/2003 | Reinemann et al. |
| 6,558,390 B2 | 5/2003 | Cragg |
| 6,562,043 B1 | 5/2003 | Chan |
| 6,568,313 B2 | 5/2003 | Fukui et al. |
| 6,569,167 B1 | 5/2003 | Bobechko et al. |
| 6,569,187 B1 | 5/2003 | Bonutti |
| 6,572,635 B1 | 6/2003 | Bonutti |
| 6,575,980 B1 | 6/2003 | Robie et al. |
| 6,575,982 B1 | 6/2003 | Bonutti |
| D477,776 S | 7/2003 | Pontaoe |
| 6,585,750 B2 | 7/2003 | Bonutti |
| 6,585,764 B2 | 7/2003 | Wright et al. |
| 6,589,248 B1 | 7/2003 | Hughes |
| 6,589,281 B2 | 7/2003 | Hyde, Jr. |
| 6,592,531 B2 | 7/2003 | Bonutti |
| 6,592,609 B1 | 7/2003 | Bonutti |
| 6,594,517 B1 | 7/2003 | Nevo |
| 6,605,090 B1 | 8/2003 | Trieu |
| 6,607,534 B2 | 8/2003 | Bonutti |
| 6,610,080 B2 | 8/2003 | Morgan |
| 6,616,696 B1 | 9/2003 | Merchant |
| 6,618,910 B1 | 9/2003 | Pontaoe |
| 6,620,181 B1 | 9/2003 | Bonutti |
| 6,623,486 B1 | 9/2003 | Weaver |
| 6,623,487 B1 | 9/2003 | Goshert |
| 6,626,944 B1 | 9/2003 | Taylor |
| 6,630,000 B1 | 10/2003 | Bonutti |
| 6,632,245 B2 | 10/2003 | Kim |
| 6,635,073 B2 | 10/2003 | Bonutti |
| 6,638,279 B2 | 10/2003 | Bonutti |
| 6,638,309 B2 | 10/2003 | Bonutti |
| 6,641,592 B1 | 11/2003 | Sauer et al. |
| 6,645,227 B2 | 11/2003 | Fallin et al. |
| 6,652,532 B2 | 11/2003 | Bonutti |
| 6,652,587 B2 | 11/2003 | Felt et al. |
| 6,666,877 B2 | 12/2003 | Morgan et al. |

(56) References Cited

U.S. PATENT DOCUMENTS

| | | |
|---|---|---|
| 6,669,705 B2 | 12/2003 | Westhaver et al. |
| 6,679,888 B2 | 1/2004 | Green et al. |
| 6,685,750 B1 | 2/2004 | Plos et al. |
| 6,699,240 B2 * | 3/2004 | Francischelli .................. 606/32 |
| 6,702,821 B2 | 3/2004 | Bonutti |
| 6,702,856 B2 | 3/2004 | Bonutti |
| 6,705,179 B1 | 3/2004 | Mohtasham |
| 6,709,457 B1 | 3/2004 | Otte |
| 6,719,765 B2 * | 4/2004 | Bonutti ........................ 606/148 |
| 6,719,797 B1 | 4/2004 | Ferree |
| 6,719,803 B2 | 4/2004 | Bonutti |
| 6,722,552 B2 | 4/2004 | Fenton |
| 6,723,102 B2 | 4/2004 | Johnson et al. |
| 6,733,506 B1 | 5/2004 | McDevitt et al. |
| 6,733,531 B1 | 5/2004 | Trieu |
| 6,736,853 B2 | 5/2004 | Bonutti |
| 6,755,865 B2 | 6/2004 | Tarabishy |
| 6,764,514 B1 | 7/2004 | Li et al. |
| 6,770,078 B2 | 8/2004 | Bonutti |
| 6,776,753 B1 | 8/2004 | Holcomb |
| 6,776,938 B2 | 8/2004 | Bonutti |
| 6,779,871 B1 | 8/2004 | Seto |
| 6,780,198 B1 | 8/2004 | Gregoire et al. |
| 6,786,989 B2 | 9/2004 | Torriani et al. |
| 6,796,003 B1 | 9/2004 | Marvel |
| 6,796,973 B1 | 9/2004 | Contente |
| 6,818,010 B2 | 11/2004 | Eichhorn et al. |
| 6,823,871 B2 | 11/2004 | Schmieding |
| 6,827,723 B2 | 12/2004 | Carson |
| 6,835,198 B2 | 12/2004 | Bonutti |
| 6,849,076 B2 | 2/2005 | Blunn |
| 6,860,885 B2 | 3/2005 | Bonutti |
| 6,860,904 B2 | 3/2005 | Bonutti |
| 6,878,167 B2 | 4/2005 | Ferree |
| 6,890,334 B2 | 5/2005 | Brace et al. |
| 6,893,434 B2 | 5/2005 | Fenton et al. |
| 6,899,722 B2 | 5/2005 | Bonutti |
| 6,905,517 B2 | 6/2005 | Bonutti |
| 6,908,466 B1 | 6/2005 | Bonutti et al. |
| 6,911,754 B2 | 6/2005 | Johnson |
| 6,913,666 B1 | 7/2005 | Aeschlimann et al. |
| 6,916,321 B2 | 7/2005 | TenHuisen |
| 6,921,264 B2 | 7/2005 | Mayer et al. |
| 6,923,824 B2 | 8/2005 | Morgan et al. |
| 6,932,835 B2 | 8/2005 | Bonutti |
| 6,942,684 B2 | 9/2005 | Bonutti |
| 6,944,111 B2 | 9/2005 | Nakamura et al. |
| 6,955,172 B2 | 10/2005 | Nelson |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt et al. |
| 6,989,029 B2 | 1/2006 | Bonutti |
| 6,990,982 B1 | 1/2006 | Bonutti |
| 6,997,940 B2 | 2/2006 | Bonutti |
| 7,001,385 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,018,380 B2 | 3/2006 | Cole |
| 7,029,432 B2 | 4/2006 | Woo |
| 7,033,379 B2 | 4/2006 | Peterson |
| 7,048,741 B2 | 5/2006 | Swanson |
| 7,048,755 B2 | 5/2006 | Bonutti |
| 7,066,960 B1 | 6/2006 | Dickman |
| 7,070,557 B2 | 7/2006 | Bonutti |
| 7,087,073 B2 | 8/2006 | Bonutti |
| 7,090,111 B2 | 8/2006 | Egan et al. |
| 7,094,251 B2 | 8/2006 | Bonutti |
| 7,101,374 B2 | 9/2006 | Hyde |
| 7,104,996 B2 | 9/2006 | Bonutti |
| 7,114,500 B2 | 10/2006 | Bonutti |
| 7,128,753 B1 | 10/2006 | Bonutti et al. |
| 7,128,763 B1 | 10/2006 | Blatt |
| 7,134,437 B2 | 11/2006 | Bonutti |
| 7,147,652 B2 | 12/2006 | Bonutti et al. |
| 7,153,312 B1 | 12/2006 | Torrie et al. |
| 7,160,405 B2 | 1/2007 | Aeschlimann et al. |
| 7,179,259 B1 | 2/2007 | Gibbs |
| 7,192,448 B2 | 3/2007 | Ferree |
| 7,195,645 B2 | 3/2007 | Disilvestro |
| 7,208,013 B1 | 4/2007 | Bonutti |
| 7,217,273 B2 | 5/2007 | Bonutti |
| 7,217,279 B2 | 5/2007 | Reese |
| 7,217,290 B2 | 5/2007 | Bonutti |
| 7,241,297 B2 | 7/2007 | Shaolian et al. |
| 7,250,051 B2 * | 7/2007 | Francischelli .................. 606/51 |
| 7,252,685 B2 | 8/2007 | Bindseil et al. |
| 7,273,497 B2 | 9/2007 | Ferree |
| 7,311,719 B2 | 12/2007 | Bonutti |
| 7,329,263 B2 | 2/2008 | Bonutti |
| 7,335,205 B2 | 2/2008 | Aeshcliamann |
| 7,371,240 B2 | 5/2008 | Pinczewski et al. |
| 7,429,266 B2 | 9/2008 | Bonutti |
| 7,445,634 B2 | 11/2008 | Trieu |
| 7,462,200 B2 | 12/2008 | Bonutti |
| 7,481,825 B2 | 1/2009 | Bonutti |
| 7,481,831 B2 | 1/2009 | Bonutti |
| 7,510,895 B2 | 3/2009 | Raterman |
| 7,610,557 B2 | 10/2009 | McLennan et al. |
| 7,615,054 B1 | 11/2009 | Bonutti |
| 7,635,390 B1 | 12/2009 | Bonutti |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,780,670 B2 | 8/2010 | Bonutti |
| 7,806,896 B1 | 10/2010 | Bonutti |
| 7,806,897 B1 | 10/2010 | Bonutti |
| 7,828,852 B2 | 11/2010 | Bonutti |
| 7,837,736 B2 | 11/2010 | Bonutti |
| 7,854,750 B2 | 12/2010 | Bonutti |
| 7,879,072 B2 | 2/2011 | Bonutti |
| 7,891,691 B2 | 2/2011 | Bearey |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,959,635 B1 | 6/2011 | Bonutti |
| 7,967,820 B2 | 6/2011 | Bonutti |
| 8,092,462 B2 | 1/2012 | Pinczewski et al. |
| 8,128,669 B2 | 3/2012 | Bonutti |
| 8,133,229 B1 | 3/2012 | Bonutti |
| 8,140,982 B2 | 3/2012 | Hamilton, II et al. |
| 8,147,514 B2 | 4/2012 | Bonutti |
| 8,162,977 B2 | 4/2012 | Bonutti et al. |
| 8,425,522 B2 | 4/2013 | Bonutti |
| 8,486,066 B2 | 7/2013 | Bonutti |
| 2001/0002440 A1 | 5/2001 | Bonutti |
| 2001/0009250 A1 | 7/2001 | Herman et al. |
| 2001/0023371 A1 | 9/2001 | Bonutti |
| 2001/0029400 A1 | 10/2001 | Deffenbaugh |
| 2001/0041916 A1 | 11/2001 | Bonutti |
| 2002/0016593 A1 | 2/2002 | Hearn et al. |
| 2002/0016633 A1 | 2/2002 | Lin et al. |
| 2002/0019649 A1 | 2/2002 | Sikora |
| 2002/0026244 A1 | 2/2002 | Trieu |
| 2002/0029055 A1 | 3/2002 | Bonutti |
| 2002/0029083 A1 | 3/2002 | Zucherman et al. |
| 2002/0029084 A1 | 3/2002 | Paul et al. |
| 2002/0032484 A1 | 3/2002 | Hyde |
| 2002/0040246 A1 | 4/2002 | Bonutti |
| 2002/0045902 A1 | 4/2002 | Bonutti |
| 2002/0062153 A1 | 5/2002 | Paul et al. |
| 2002/0066450 A1 | 6/2002 | Bonutti |
| 2002/0095160 A1 | 7/2002 | Bonutti |
| 2002/0103495 A1 | 8/2002 | Cole |
| 2002/0123750 A1 | 9/2002 | Eisermann et al. |
| 2002/0138150 A1 | 9/2002 | Leclercq |
| 2002/0183762 A1 | 12/2002 | Anderson et al. |
| 2002/0188301 A1 | 12/2002 | Dallara et al. |
| 2003/0009147 A1 | 1/2003 | Bonutti |
| 2003/0023260 A1 | 1/2003 | Bonutti |
| 2003/0032975 A1 | 2/2003 | Bonutti |

(56) References Cited

U.S. PATENT DOCUMENTS

| | | |
|---|---|---|
| 2003/0039196 A1 | 2/2003 | Nakamura et al. |
| 2003/0040758 A1 | 2/2003 | Wang et al. |
| 2003/0065361 A1 | 4/2003 | Dreyfuss |
| 2003/0105474 A1 | 6/2003 | Bonutti |
| 2003/0118518 A1 | 6/2003 | Hahn et al. |
| 2003/0158582 A1 | 8/2003 | Bonutti et al. |
| 2003/0167072 A1 | 9/2003 | Oberlander |
| 2003/0181800 A1 | 9/2003 | Bonutti |
| 2003/0195530 A1 | 10/2003 | Thill |
| 2003/0195565 A1 | 10/2003 | Bonutti |
| 2003/0204204 A1 | 10/2003 | Bonutti |
| 2003/0216742 A1 | 11/2003 | Wetzler et al. |
| 2003/0225438 A1 | 12/2003 | Bonutti et al. |
| 2003/0229361 A1 | 12/2003 | Jackson |
| 2003/0236572 A1 | 12/2003 | Bertram |
| 2004/0010287 A1 | 1/2004 | Bonutti |
| 2004/0030341 A1 | 2/2004 | Aeschlimann et al. |
| 2004/0034357 A1 | 2/2004 | Beane et al. |
| 2004/0059423 A1 | 3/2004 | Barnes |
| 2004/0097794 A1 | 5/2004 | Bonutti |
| 2004/0097939 A1 | 5/2004 | Bonutti |
| 2004/0098016 A1 | 5/2004 | Bonutti |
| 2004/0098050 A1 | 5/2004 | Foerster et al. |
| 2004/0127930 A1 | 7/2004 | Bonutti |
| 2004/0138689 A1 | 7/2004 | Bonutti |
| 2004/0138690 A1 | 7/2004 | Bonutti |
| 2004/0138703 A1 | 7/2004 | Alleyne |
| 2004/0143285 A1 | 7/2004 | Bonutti |
| 2004/0143334 A1 | 7/2004 | Ferree |
| 2004/0167548 A1 | 8/2004 | Bonutti |
| 2004/0172033 A1 | 9/2004 | Bonutti |
| 2004/0193181 A1 | 9/2004 | Bonutti |
| 2004/0193266 A1 | 9/2004 | Meyer |
| 2004/0220616 A1 | 11/2004 | Bonutti |
| 2004/0225325 A1 | 11/2004 | Bonutti |
| 2004/0230223 A1 | 11/2004 | Bonutti |
| 2004/0236374 A1 | 11/2004 | Bonutti et al. |
| 2004/0254582 A1 | 12/2004 | Bonutti |
| 2005/0033366 A1 | 2/2005 | Cole |
| 2005/0038514 A1 | 2/2005 | Helm et al. |
| 2005/0043796 A1 | 2/2005 | Grant et al. |
| 2005/0071012 A1 | 3/2005 | Serhan et al. |
| 2005/0090827 A1 | 4/2005 | Gedebou |
| 2005/0096699 A1 | 5/2005 | Wixey et al. |
| 2005/0113928 A1 | 5/2005 | Cragg et al. |
| 2005/0126680 A1 | 6/2005 | Aeschlimann et al. |
| 2005/0143826 A1 | 6/2005 | Zucherman et al. |
| 2005/0149024 A1 | 7/2005 | Ferrante et al. |
| 2005/0149029 A1 | 7/2005 | Bonutti |
| 2005/0203521 A1 | 9/2005 | Bonutti |
| 2005/0216059 A1 | 9/2005 | Bonutti |
| 2005/0216087 A1 | 9/2005 | Zucherman et al. |
| 2005/0222620 A1 | 10/2005 | Bonutti |
| 2005/0234555 A1 | 10/2005 | Sutton |
| 2005/0240190 A1 | 10/2005 | Gall et al. |
| 2005/0240227 A1 | 10/2005 | Bonutti |
| 2005/0246021 A1 | 11/2005 | Ringeisen et al. |
| 2005/0251080 A1 | 11/2005 | Hyde |
| 2005/0256571 A1 | 11/2005 | Azar |
| 2005/0261684 A1 | 11/2005 | Shaolian et al. |
| 2005/0267481 A1 | 12/2005 | Carl et al. |
| 2005/0267534 A1 | 12/2005 | Bonutti |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0036323 A1 | 2/2006 | Carl |
| 2006/0047283 A1 | 3/2006 | Evans |
| 2006/0058790 A1 | 3/2006 | Carl |
| 2006/0064095 A1 | 3/2006 | Senn et al. |
| 2006/0089646 A1 | 4/2006 | Bonutti |
| 2006/0122600 A1 | 6/2006 | Cole |
| 2006/0122704 A1 | 6/2006 | Vresilovic et al. |
| 2006/0142799 A1 | 6/2006 | Bonutti |
| 2006/0149277 A1 | 7/2006 | Cinquin |
| 2006/0149338 A1 | 7/2006 | Flaherty |
| 2006/0167495 A1 | 7/2006 | Bonutti |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti |
| 2006/0235470 A1 | 10/2006 | Bonutti |
| 2006/0241695 A1 | 10/2006 | Bonutti |
| 2006/0247782 A1 | 11/2006 | Molz |
| 2006/0265009 A1 | 11/2006 | Bonutti |
| 2006/0265011 A1 | 11/2006 | Bonutti |
| 2007/0032825 A1 | 2/2007 | Bonutti et al. |
| 2007/0050030 A1 | 3/2007 | Kim |
| 2007/0088362 A1 | 4/2007 | Bonutti et al. |
| 2007/0100457 A1 | 5/2007 | Hyde |
| 2007/0102005 A1 | 5/2007 | Bonutti |
| 2007/0118129 A1 | 5/2007 | Fraser et al. |
| 2007/0179493 A1 | 8/2007 | Kim |
| 2007/0198555 A1 | 8/2007 | Friedman et al. |
| 2007/0208378 A1 | 9/2007 | Bonutti et al. |
| 2007/0265561 A1 | 11/2007 | Yeung |
| 2007/0270833 A1 | 11/2007 | Bonutti |
| 2008/0021474 A1 | 1/2008 | Bonutti |
| 2008/0039845 A1 | 2/2008 | Bonutti |
| 2008/0039873 A1 | 2/2008 | Bonutti |
| 2008/0046090 A1 | 2/2008 | Paul et al. |
| 2008/0047567 A1 | 2/2008 | Bonutti |
| 2008/0051799 A1 | 2/2008 | Bonutti |
| 2008/0058822 A1 | 3/2008 | Bonutti |
| 2008/0065140 A1 | 3/2008 | Bonutti |
| 2008/0097448 A1 | 4/2008 | Binder et al. |
| 2008/0103519 A1 | 5/2008 | Bonutti |
| 2008/0108897 A1 | 5/2008 | Bonutti et al. |
| 2008/0108916 A1 | 5/2008 | Bonutti |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | Bonutti |
| 2008/0195145 A1 | 8/2008 | Bonutti |
| 2008/0269753 A1 | 10/2008 | Cannestra |
| 2008/0269808 A1 | 10/2008 | Gall et al. |
| 2009/0024161 A1 | 1/2009 | Bonutti |
| 2009/0093684 A1 | 4/2009 | Schorer |
| 2009/0138014 A1 | 5/2009 | Bonutti |
| 2009/0194969 A1 | 8/2009 | Bearey |
| 2010/0211120 A1 | 8/2010 | Bonutti |
| 2010/0312350 A1 | 12/2010 | Bonutti |
| 2011/0060375 A1 | 3/2011 | Bonutti |
| 2011/0295253 A1 | 12/2011 | Bonutti et al. |
| 2012/0010623 A1 | 1/2012 | Bonutti |
| 2012/0165841 A1 | 6/2012 | Bonutti |
| 2012/0191140 A1 | 7/2012 | Bonutti |
| 2012/0215226 A1 | 8/2012 | Bonutti |
| 2012/0215233 A1 | 8/2012 | Bonutti et al. |
| 2012/0221017 A1 | 8/2012 | Bonutti |
| 2013/0144389 A1 | 6/2013 | Bonutti |
| 2013/0197542 A1 | 8/2013 | Bonutti |
| 2013/0197543 A1 | 8/2013 | Bonutti |
| 2013/0204272 A1 | 8/2013 | Bonutti |
| 2013/0226185 A1 | 8/2013 | Bonutti |
| 2013/0226311 A1 | 8/2013 | Bonutti |

FOREIGN PATENT DOCUMENTS

| | | |
|---|---|---|
| CA | 2698057 | 3/2009 |
| DE | 1903016 | 10/1964 |
| DE | 1903316 | 10/1964 |
| DE | 1903016 | 8/1970 |
| DE | 3517204 | 11/1986 |
| DE | 3722538 | 1/1989 |
| DE | 9002844 U1 | 1/1991 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |

(56) References Cited

FOREIGN PATENT DOCUMENTS

| | | |
|---|---|---|
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 91/12779 | 9/1991 |
| WO | 93/23094 | 11/1993 |
| WO | WO9408642 | 4/1994 |
| WO | 95/16398 | 6/1995 |
| WO | WO 95/31941 | 11/1995 |
| WO | WO9614802 | 5/1996 |
| WO | WO9712779 | 4/1997 |
| WO | 97/49347 | 12/1997 |
| WO | WO 97/49347 | 12/1997 |
| WO | WO9811838 | 3/1998 |
| WO | WO9826720 | 6/1998 |
| WO | WO02053011 | 7/2002 |
| WO | 2007/092869 | 8/2007 |
| WO | 2007/092869 A2 | 8/2007 |
| WO | 2008/116203 | 9/2008 |
| WO | 2009/029908 | 3/2009 |
| WO | 2009124215 | 10/2009 |
| WO | WO2010099222 | 2/2010 |

OTHER PUBLICATIONS

IPR—International Publication WO/2008/116203, published Sep. 22, 2009 for PCT/US08/57948.
ISR—International Search Report WO/2008/116203, published Dec. 24, 2008 for PCT/US08/57948.
IPER—Internation Preliminary Report on Patentability, WO/2008/116203, published Sep. 22, 2009 for PCT/US08/57948.
Written Opinion WO/2008/116203 dated Oct. 23, 2008 for PCT/US08/57948.
IPR—International Publication WO2009/029908, published May 3, 2009 for PCT/US08/74941.
ISR—International Search Report, WO2009/029908, published May 3, 2009 for PCT/US08/74941.
IPER—Internation Preliminary Report on Patentability, WO2009/029908, published Mar. 2, 2010 for PCT/US08/74941.
Written Opinion WO2009/029908 dated Feb. 28, 2010 for PCT/US08/74941.
International Search Report PCT/US2010/025263 completed Apr. 13, 2010.
Written Opinion for PCT/US2010/025263 completed Apr. 13, 2010.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Branson, Polymers: Characteristics and Compatibility for Ultrasonic Assembly, Applied Technologies Group, Publication unknown, date unknown.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Copr., (c) 1992.
IPR—International Publication WO/2007/092869, published Aug. 16, 2007 for PCT/US2007/061730.
ISR—International Search Report WO/2007/092869, published Dec. 13, 2007 for PCT/US2007/061730.
Intl Prelim Report on Patentability, WO/2007/092869, published Aug. 12, 2008 for PCT/US2007/061730.
Written Opinion WO/2007/092869 dated Aug. 7, 2008 for PCT/US2007/061730.
010-3 Copending U.S. Appl. No. 11/932,907—RCE Response Sep. 15, 2011.
027 Copending U.S. Appl. No. 11/258,795 Non-Final Office Action mailed Apr. 26, 2011.
046 Copending U.S. Appl. No. 11/689,670, RCE Response Sep. 19, 2011.
European Search Report dated Sep. 10, 2012 for EP08732724.3 (046).
003-1 Copending U.S. Appl. No. 10/614,352, Final Office Action Jul. 12, 2010.
007-2 Copending U.S. Appl. No. 11/932,602 Final Response to Office Action Jun. 10, 2011.
039 Copending U.S. Appl. No. 11/671,556, Response filed Aug. 23, 2010.
Co-pending U.S. Appl. No. 11/438,537, Supplemental Final Rejection mailed Sep. 25, 2009.
Petition for Inter Partes Review of U.S. Pat. No. 5,980,559, IPR 2013-00603, Filing Date Sep. 24, 2013.
Declaration of David Kaplan, PH.D. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013, Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013.
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013.
Flory, Principles of Polymer Chemistry, 1953, selected pages.
Grizzi, Hydrolytic degradation of devices based on poly(DL-lactic acid) size-dependence, Biomaterials, 1995, vol. 16, No. 4, p. 305-311.
Gopferich, Mechanisms of polymer degradation and erosion, Biomaterials, 1996, vol. 17, No. 2, p. 103-114.
Gao et el, Swelling of Hydroxypropyl Methylcellulose Matrix Tablets . . . , J. of Pharmaceutical Sciences, vol. 85, No. 7, Jul. 1996, p. 732-740.
Linvatec, Impact Suture Anchor brochure, 2004.

(56) References Cited

OTHER PUBLICATIONS

Seitz et al, Repair of the Tibiofibular Syndesmosis with a Flexible Implant, J. of Orthopaedic Trauma, vol. 5, No. 1, p. 78-82, 1991.
Translation of FR2696338 with translator's certificate dated Sep. 17, 2013.
Translation of DE9002844.9 with translator's certificate dated Sep. 26, 2013.
Declaration of Steve Jordan for U.S. Pat. No. 5,921,986, from IPR 2013-00632, dated Sep. 24, 2013.
Declaration of Steve Jordan for U.S. Pat. No. 5,921,986, from IPR 2013-00633, dated Sep. 24, 2013.
Declaration of Dr. Steve E. Jordan for U.S. Pat. No. 8,147,514, from IPR 2013-00631, dated Sep. 23, 2013.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 1995, Arthroscopy vol. 11 No. 2 p. 245-251.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64—Feb. 1998.
Packer et al, Repair of Acute Scapho-Lunate Dissociation Facilitated by the "Tag"* Suture Anchor, Journal of Hand Surgery (British and European vol. 1994) 19B: 5: 563-564.
Richmond, Modificatio of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb.), 1998: pp. 118-122.
Tfix, Acufex just tied the knot . . . , Am. J. Sports Med., vol. 22, No. 3, May-Jun. 1994.
Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 (Feb.), 2010: pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger, et al, Radial avulsion of the triangular fibrocartilage complex in acute wrist trauma: a new technique for arthroscopic repair, Jun. 1997, Arthroscopy vol. 13 No. 3 p. 370-374.
Hecker et al , Pull-out strength of suture anchors for rotator cuff and Bankart lesion repairs, Nov.-Dec. 1993, The American Journal of Sports Medicine, vol. 21 No. 6 p. 874-879.
Hernigou et al , Proximal Tibial Osteotomy for Osteoarthritis with Varus Deformity a Ten to Thirteen-Year Follow-Up Study, J Bone Joint Surg, vol. 69-A, No. 3. Mar. 1987, p. 332-354.
Ibarra et al, Glenoid Replacement in Total Shoulder Arthroplasty, The Orthopedic Clinics of NorthAmerica: Total Shoulder Arthroplasty, vol. 29 No. 3, Jul. 1998 p. 403-413.
Mosca et al, Calcaneal Lengthening for Valgus Deformity of the Hindfoot: Results in Children Who Had Severe, Symptomatic fLATFOOT and Skewfoot, J Bone Joint Surg., 1195—p. 499-512.
Murphycet al , Radial Opening Wedge Osteotomy in Madelung's Deformity, J. Hand Surg, vol. 21 A No. 6 Nov. 1996, p. 1035-1044.
Biomet, Stanmore Modular Hip, J. Bone Joint Surg., vol. 76-B : No. Two, Mar. 1994.
Intl Prelim Rep on Patentability and Written Opinion for PCT/US10/25263 dated Aug. 30, 2011.

* cited by examiner

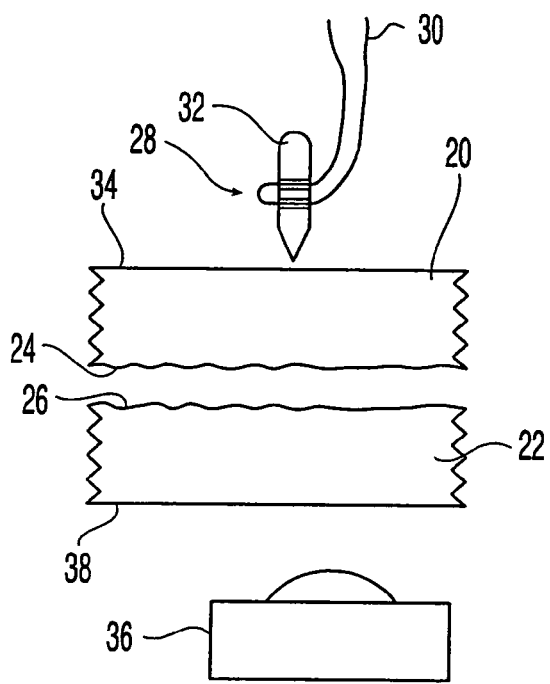
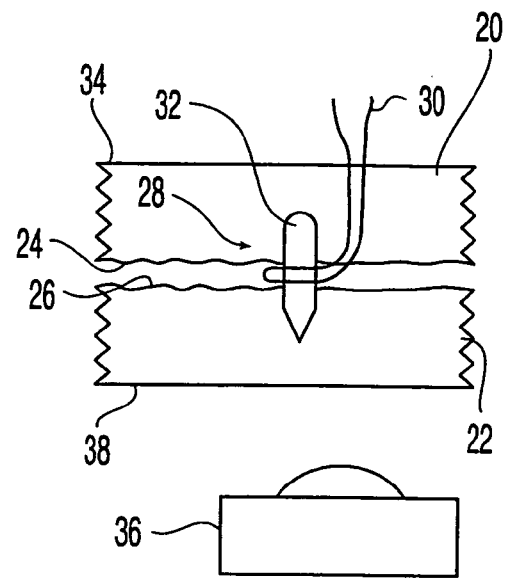
*Fig. 1*  *Fig. 2*
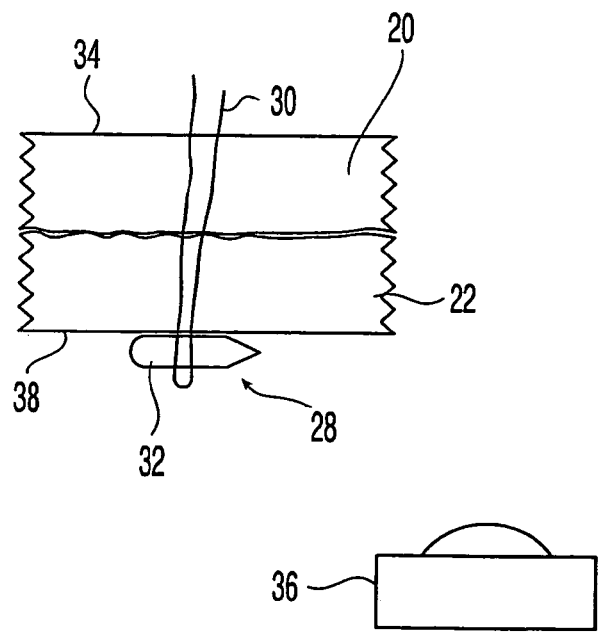
*Fig. 3*

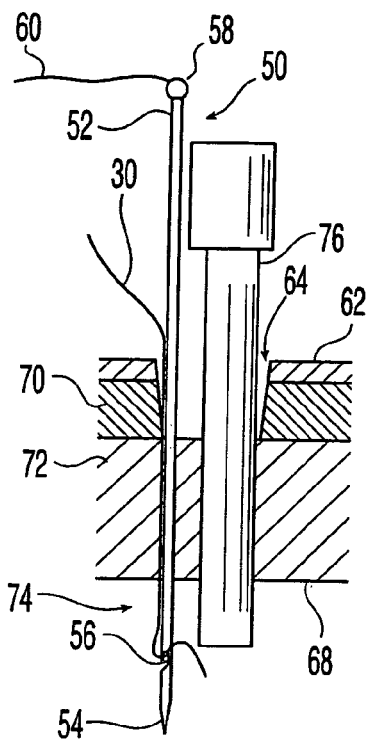
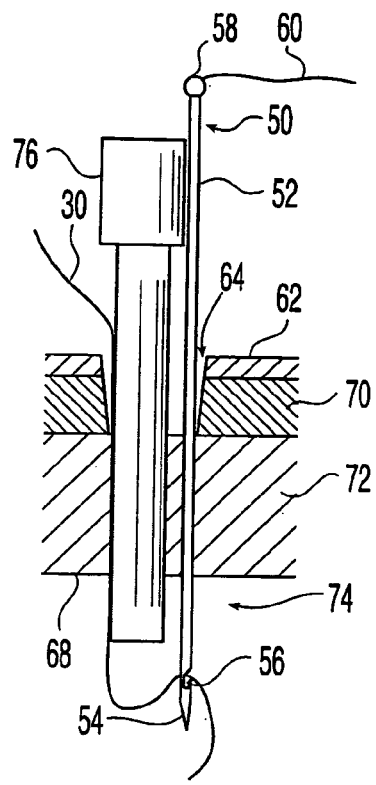
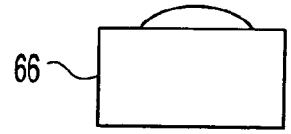
Fig. 4
Fig. 5
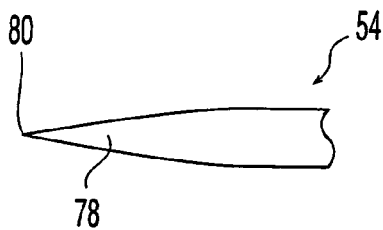
Fig. 6
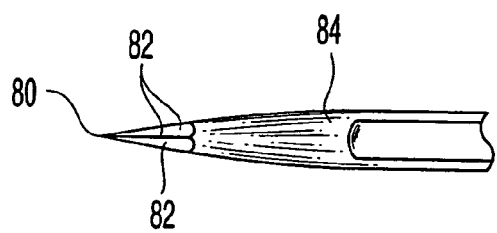
Fig. 7
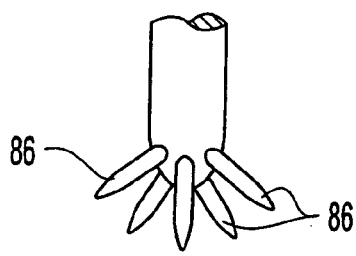
Fig. 8

MAGNETIC POSITIONING APPARATUS

CROSS-REFERENCE TO RELATED APPLICATION

This application is a continuation of U.S. patent application Ser. No. 10/005,652, filed on Dec. 2, 2001, which resulted in U.S. Pat. No. 6,719,765, issued on Apr. 13, 2004.

FIELD OF THE INVENTION

The present invention relates to an instrument and method for passing a medical implement, such as suture or similar element, through tissue.

BACKGROUND OF THE INVENTION

The insertion of a medical instrument or implant through tissue can involve the application of significant mechanical force. For example, the insertion of a suture through thick connective tissue requires substantial pressure, regardless of whether the suture is pushed or pulled through the tissue. In an open surgical procedure, the exposure of the large surgical incision provides access for manipulation and visualization. Nevertheless, insertion can still be problematic. Furthermore, it is often desirable to minimize the size of this incision to reduce scarring and soft tissue trauma.

Arthroscopy and other minimally invasive surgical procedures utilize small incisions or portals for insertion of diagnostic and surgical instruments manipulated externally of the body, and therefore, avoid the trauma associated with large incisions as well as the hospitalization and prolonged recovery periods required with open surgery. While it is not always required, an endoscope may be used to enhance visualization. However, due to the small surgical incision of these minimally invasive approaches, it is frequently difficult to gain the access required to insert and manipulate the instrument or implant. Remotely passing a suture through tissue can be one particularly troublesome task.

The prior art teaches a number of devices attempting to solve this problem. For example, the Carter-Thomason suture passer disclosed in U.S. Pat. No. 5,496,335 has a sharp tip that opens and closes so that the tip can both grasp the suture and penetrate through tissue. However, this instrument, like most, if not all, relies solely on mechanical force to pass the suture through tissue.

Thus, there exists a need for an improved suture inserter and method.

SUMMARY OF THE INVENTION

The present invention relates to a method of passing a medical implement having a magnetic component through tissue. The medical implement is placed on a first side of the tissue, a magnetic field is established on a second side of the tissue, and at least one of the magnetic component and magnetic field is manipulated to drive the medical implement through the tissue. In one embodiment, the magnetic component is a portion of the medical implement. Alternatively, the magnetic component can be attached to the medical implement.

The magnetic component can be made of a magnetizable material, or can actually be a magnet, either a permanent magnet or an electromagnet. Regardless of the nature of the magnetic component, the magnetic field location can be altered to provide directional control of the medical implement as it is driven through the tissue. In an exemplary embodiment, the medical implement is made of a non-magnetic matrix and the magnetic component is dispersed within the matrix material. The matrix can be a resorbable material, with the magnetic component comprising a plurality of iron particles.

The present invention also relates to a surgical instrument for delivery of an implant through tissue. The implant has a body, a carrier located on the body for removeably securing at least a portion of the implant to the instrument, a tip located at a distal end of the body and configured and dimensioned for insertion through the tissue, and a magnetic element located on the body. Interaction between the magnetic element and a magnetic field external to the tissue drives the instrument through the tissue.

The magnetic element can be part of the body or attached to the body. The magnetic element can be a permanent magnet or an electromagnet. Regardless, the magnetic element can be movable to provide directional control of the instrument as it is driven through the tissue.

The invention is also related to a suture passer for inserting a suture through tissue. The suture passer includes an elongate body having proximal and distal ends, a first jaw disposed on the distal end of the body and having a first magnetic element, and a second jaw disposed on the distal end of the body and having a second magnetic element. At least one of the first and second magnetic elements is an electromagnet and the other can be made of a magnetizable material. A handle is disposed on the proximal end of the body for manipulation of the suture passer and a controller is provided for operating the electromagnet. The first and second jaws are movable relative to each other from a closed position to an open position and one of the polarity and strength of the electromagnet is changed to move the first and second jaws to the open and closed positions.

In one embodiment, the first jaw has a piercer for penetrating the tissue and the second jaw has an opening for receiving the piercer. The handle can be operated to move the first and second jaws to the open and closed positions. The piercer can be provided with an opening for receiving the suture so that the suture can be passed through the tissue after the piercer has penetrated the tissue. In an exemplary embodiment, the first magnetic element is the piercer and the first and second jaws are slideable with respect to one another to vary the angle the piercer is inserted through the tissue.

In another embodiment, the first jaw has a clip for holding a suture needle. Again, the handle can be operated to move the first and second jaws to the open and closed positions.

Both the first and second magnetic elements can be electromagnets. Accordingly, the first and second electromagnets can be selectively activatable and deactivatable to move an implant back and forth through tissue. A mechanical stop can be provided on either or both of the jaws to removeably secure the implant to the jaw. The mechanical stop can be either independent of the controller for the electromagnet or can be operated by the controller.

In use, a suture needle, with suture attached thereto, is removeably secured to the first jaw of the suture passer. A portion of the body of the suture passer is inserted through an incision in a patient so that the first and second jaws are located adjacent the tissue. The first and second jaws are separated to the open position so that the first jaw is on a first side of the tissue and the second jaw is on a second side of the tissue and the controller is operated to move the first and second jaws to the closed position so that the needle tip penetrates the tissue. After the needle penetrates the tissue, the needle can be released from the first jaw; and pulled through to thereby pass the suture through the tissue. If desired, the needle can be removeably secured to the second jaw to pass the needle back and forth through the tissue.

The suture passer can also be used by providing the first jaw with a piercer for penetrating the tissue and providing the second jaw with an opening for receiving the piercer. At least a portion of the body of the suture passer is inserted through an incision in a patient so that the first and second jaws are located adjacent the tissue. The first and second jaws are separated to the open position so that the first jaw is on a first side of the tissue and the second jaw is on a second side of the tissue. The controller is operated to move the first and second jaws to the closed position so that the tip penetrates the tissue. The suture is then fed through a bore in the piercer.

BRIEF DESCRIPTION OF THE DRAWINGS

Preferred features of the present invention are disclosed in the accompanying drawings, wherein similar reference characters denote similar elements throughout the several views, and wherein:

FIG. 1 schematically shows an embodiment of the present invention, in the form of a suture anchor and an external magnetic field generator, prior to insertion in first and second tissue sections;

FIG. 2 shows the suture anchor of FIG. 1 inserted between first and second tissue sections;

FIG. 3 shows the suture anchor of FIG. 1 completely inserted through the second tissue section;

FIG. 4 schematically shows another embodiment of the present invention, in the form of a suture passer and an external magnetic field generator, inserted in the tissue at a first location;

FIG. 5 shows the suture passer of FIG. 4 re-inserted in the tissue at a second location;

FIG. 6 shows one embodiment of a tip for penetrating tissue;

FIG. 7 shows another embodiment of a tip for penetrating tissue;

FIG. 8 shows another embodiment of a tip for penetrating tissue;

DETAILED DESCRIPTION OF THE INVENTION

Figure 9:
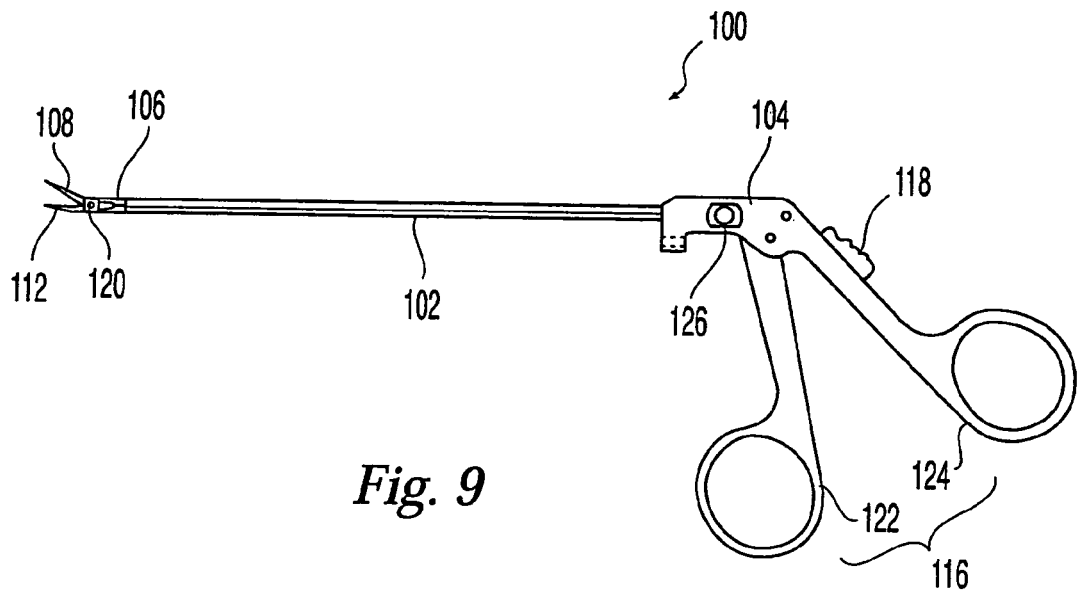
FIG. 9 shows another embodiment of the present invention, in the form of a suture passer.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto. Finally, any reference to a particular biological application, such as fixation with a suture anchor, is simply used for convenience as one example of a possible use for the invention and is not intended to limit the scope of the present invention thereto.

FIGS. 1-3 schematically show one embodiment of the present invention. First and second tissue sections 20, 22 are to be brought into close apposition. Specifically, surface 24 of first tissue section 20 and surface 26 of second tissue section 22 are to be placed in contact. A medical implement, in the form of a suture anchor 28 is provided in this regard. Suture anchor 28 can be used in a wide variety of applications including rotator cuff repair, heart valve replacement and repair, vessel repair and replacement, hernia repair, anastomosis, and other procedures.

Suture anchor 28 includes a flexible suture 30 so that in order to join first and second tissue sections 20, 22, suture anchor 28 passes from first tissue section 20 through second tissue section 22 with suture 30 extending across surfaces 24, 26. Suture 30 is then pulled tight to draw surfaces 24, 26 into contact and a knot or other tension retaining mechanism keeps surfaces 24, 26 in contact. Examples of methods and apparatuses for securing suture that can be used are taught in U.S. Pat. No. 6,231,592 B1, the contents of which are incorporated herein by reference. A transducer or other tension-measuring device can be used to monitor and/or control the tension on the suture.

Under the prior art, mechanical forces are used to either push or pull suture anchor 28 from first tissue section 20 through second tissue section 22. With the present invention, suture anchor 28 is provided with a magnetic component 32. Magnetic component 32 can be a portion of suture anchor 28. Alternatively, magnetic component 32 can be permanently or removeably attached to suture anchor 28. Magnetic component 32 can be made of any magnetizable material. If the surgical implement is intended to be an implant, like suture anchor 28, magnetic component 32 should be a biocompatible material. Magnetic component 32 can be a permanent magnet, or, as discussed in more detail below with respect to FIGS. 4-6, magnetic component can be an electromagnet. Examples of permanent magnets include ferromagnetic materials such as iron, nickel, and cobalt.

In use, suture anchor 28 is placed on a first side 34 of first tissue section 20 and a magnetic field generator 36 is placed on a second side 38 of second tissue section 22. In one embodiment, magnetic field generator 36 is a permanent magnet so that the magnetic field with respect to suture anchor 28 can be varied by changing the location and orientation of the permanent magnet. In another embodiment, magnetic field generator 36 is an electromagnet and is provided with a controller for electronically varying the generated electric field. Thus, regardless of the exact nature of magnetic component 32 and magnetic field generator 36 (i.e. permanent or electromagnetic), the respective magnetic fields can be manipulated. Such manipulation can be as simple as changing the relative locations of magnetic component 32 and magnetic field generator 36 or turning the current on to the electromagnet.

As shown in FIG. 2, the magnetic attraction between magnetic component 32 of suture anchor 28 and the magnetic field of magnetic field generator 36 drives suture anchor 28 through first and second tissue sections 20, 22. Although it is envisioned that the magnetic attraction alone could drive suture anchor 28 through first and second tissue sections 20, 22, this magnetic attraction could be assisted by mechanical force, e.g. pushing or pulling suture anchor 28 in addition to the magnetic field. The desirability of this assistance will depend upon a number of factors including surgeon preference, tissue type, tissue thickness, and other similar considerations. Furthermore, it is also possible to create an optional passageway (e.g. a cannula, pre-drilling, etc.) for suture anchor 28. The cross-sectional size and depth of the passageway can be determined by the surgeon.

In addition to driving suture anchor 28, the magnetic field interactions can be used to provide directional control of suture anchor 28. An example of such control is shown in FIG. 3. Suture anchor 28 has completely penetrated second tissue section 22 and magnetic field generator 36 has been moved. This causes suture anchor 28 to turn with its longest dimension resting against second tissue section 22. If magnetic field generator 36 is moved from second side 38 to first side 34, suture anchor 28 will be driven back from second tissue section 22 through first tissue section 20. In this fashion, suture anchor 28 can be repeatedly moved across first and second tissue sections 20, 22 to thereby provide multiple suture stitches. If magnetic component 32 is a permanent magnet or electromagnet, an analogous effect of moving the surgical implement back and forth through tissue can be achieved by reversing the polarity of magnetic component 32.

As shown in FIGS. 1-3, both first and second sides 34, 38 appear readily accessible. However, it should be noted that first and second tissue sections 20, 22 can be internal tissues with intervening tissue layers such that first and second sides 34, 38 are not exposed, except for any access ports or incisions created by the surgeon.

As previously noted, magnetic component 32 can be a part of suture anchor 28. In an exemplary embodiment, suture anchor 28 is made of a non-magnetizable matrix and magnetic component 32 is dispersed within the matrix. One particularly suitable class of matrix materials is resorbable materials such as poly-lactide acid, poly-glycolic acid, combinations thereof, and other similar substances. In such cases, magnetic component 32 can be made of particles, such as iron, that are well tolerated by the body and can be removed from the body by normal physiological mechanisms, e.g. through urination, perspiration, and other excretion processes. As the matrix dissolves, the particles are naturally removed from the body with no adverse effects.

Although FIGS. 1-3 show the method according to the present invention used with a suture anchor, the method can be used with any implant that passes through tissue. Furthermore, the method can also be used with any medical instrument that passes through tissue. FIGS. 4 and 5 schematically show one such instrument.

Instrument 50 is a suture passer, used to pass a suture through tissue. Instrument 50 includes an elongate body 52 with a tip 54 located at a distal end. Tip 54 is configured and dimensioned for insertion through the tissue. Body 52 has a carrier 56 for removeably securing at least a portion of suture 30 to suture passer 50. As shown, suture carrier 56 is a slot. However, suture carrier can be other suitable mechanisms for temporally coupling the implant, in this case suture 30 to suture passer 50. Other mechanisms include an eyelet or a barb.

A magnetic element 58 is located on body 52. Magnetic element 58 can either be a part of body 52 or can be attached to body 52. As shown, magnetic element 58 is an electromagnet and wiring 60 connects the electromagnet to a power supply and controller. In use, suture 30 is connected to suture passer 50 and suture passer 50 is positioned on a first side 62 of the desired insertion site 64. An external magnetic field generator 66 is located on a second side 68 of insertion site 64. In one embodiment, magnetic field generator 66 is a permanent magnet so that the magnetic field with respect to suture passer 50 can be varied by changing the location and orientation of the permanent magnet. In another embodiment, magnetic field generator 66 is an electromagnet and is provided with a controller for electronically varying the generated electric field. Thus, regardless of the exact nature of magnetic component 58 and magnetic field generator 66 (i.e. permanent or electromagnetic), the respective magnetic fields can be manipulated. Such manipulation can be as simple as changing the relative locations of magnetic component 58 and magnetic field generator 66 or turning the current on to the electromagnet.

The magnetic attraction between magnetic component 58 of suture passer 50 and the magnetic field of magnetic field generator 66 drives suture passer 50 through skin tissue 70 and internal tissue 72 and into internal cavity 74. A trochar 76, which is ordinarily in place for percutaneous surgeries, can be used to monitor the insertion. Although it is envisioned that the magnetic attraction alone could drive suture passer 50 from first side 62 to second side 68, this magnetic attraction could be assisted by mechanical force, e.g. pushing or pulling suture passer 50 in addition to the magnetic field. The desirability of this assistance will depend upon a number of factors including surgeon preference, tissue type, tissue thickness, and other similar considerations. Furthermore, it is also possible to pre-drill an optional passageway for suture passer 50. The cross-sectional size and depth of the passageway can be determined by the surgeon.

In addition to driving suture passer 50, the magnetic field interactions can be used to provide directional control of suture passer 50. For example, the polarity of magnetic element 58 or magnetic field generator 66 can be reversed to back suture passer 50 out of internal cavity 74. Accordingly, suture 30 is uncoupled from suture passer 50; suture passer 50 is removed and re-inserted at a second location. Suture 30 is recaptured with carrier 56 and suture passer 50 is again backed out of internal cavity 74 so that both ends of suture 30 are now exposed. Suture 30 can be knotted or otherwise secured to close the insertion site.

Although FIGS. 4 and 5 show elongate body 52 extending through skin and internal tissues 70, 72, the length of elongate body 52 can be selected for a given application. For example, elongate body 52 can have a length similar to that of a conventional suture needle. Given such a length, suture passer 50 can go through the tissue in any direction and angle, dependent upon wherever guided by the magnet. Regardless of the length of elongate body 52, tip 54 can be provided with a wide variety of geometries. FIG. 6 shows a tip 54 with a conical body 78 extending to a sharp end 80. FIG. 7 shows another embodiment of a tip with beveled edges 82. Ribs 84 can be provided to facilitate insertion through tissue. FIG. 8 shows a tip that is shaped like a mace and has multiple protrusions 86 extending from its distal end. The arrangement of multiple protrusions 86 is particularly useful in allowing suture passer 50 to travel in a variety of directions.

FIG. 9 shows another embodiment of the present invention. A suture passer 100 has an elongate body 102 with proximal and distal ends 104, 106. A first jaw 108 is disposed on distal end 106 of body 102 and has a first magnetic element 110. A second jaw 112 is also disposed on distal end 106 of body 102 and has a second magnetic element 114. As previously noted with respect to the other embodiments, either or both of first and second magnetic elements 110, 114 can be a magnet or a magnetizable material. In the exemplary embodiment shown in FIG. 9, one of the magnetic elements, first magnetic element 110, is an electromagnet and second magnetic element 114 is made of a magnetizable material. This arrangement could be reversed so that second magnetic element 114 is the electromagnet and first magnetic element 110 is made of the magnetizable material. Alternatively, both first and second magnetic elements 110, 114 are electromagnets.

A handle 116 is disposed on proximal end 104 of body 102 for manipulation of suture passer 100. A controller 118 is used to control the electromagnet. If both magnetic elements 110, 114 are electromagnets, controller 118 can be configured to control both or, alternatively, a second controller can be provided. Examples of suitable controllers include a push button to simply turn the electromagnet on and off, a three way switch to turn the electromagnet on and off and control the polarity, and a three way switch with a variable resistor so the polarity and strength of the electromagnet can be adjusted. The electronic circuitry for the electromagnet is well known to those of ordinary skill of the art and can be either partially or completely location on or within suture passer 100. If any portion of the circuitry is not on suture passer 100, wiring can connect this portion to the circuitry on suture passer 100.

A pivot point 120 pivotably couples one or both of first and second jaws 108, 112 to distal end 106 of body 102 so that first and second jaws 108, 112 are moveable with respect to one another. In particular, first and second jaws 108, 112 are moveable relative to each other from a closed position, with first and second jaws 108, 112 substantially in contact if there is nothing in between first and second jaws 108, 112, to an open position, with first and second jaws 108, 112 separated from each other. An optional spring or other biasing member can be used to bias first and second jaws 108, 112 in the open or closed position.

In use, the polarity and/or strength of the electromagnet is controlled to move first and second jaws 108, 112 between the open and closed positions. For example, if second magnetic element 114 is a permanent magnet, the polarity of first magnetic element 110 can be such that there is magnetic attraction between first and second magnetic elements 110, 114 so that first and second jaws 108, 112 are in the closed position. If the polarity is changed, there is a magnetic repulsion between first and second magnetic elements 110, 114 so that first and second jaws 108, 112 are in the open position. If second magnetic element 114 is not a permanent magnet, but is rather a magnetizable element, then merely turning on the electromagnet will move first and second jaws 108, 112 to the closed position. As previously noted, a spring or other biasing member can be used to bias first and second jaws 108, 112 in the closed position so that when the electromagnet is turned off, or sufficiently reduced in magnetic strength, first and second jaws 108, 112 move from the open to the closed position.

Figure 10:
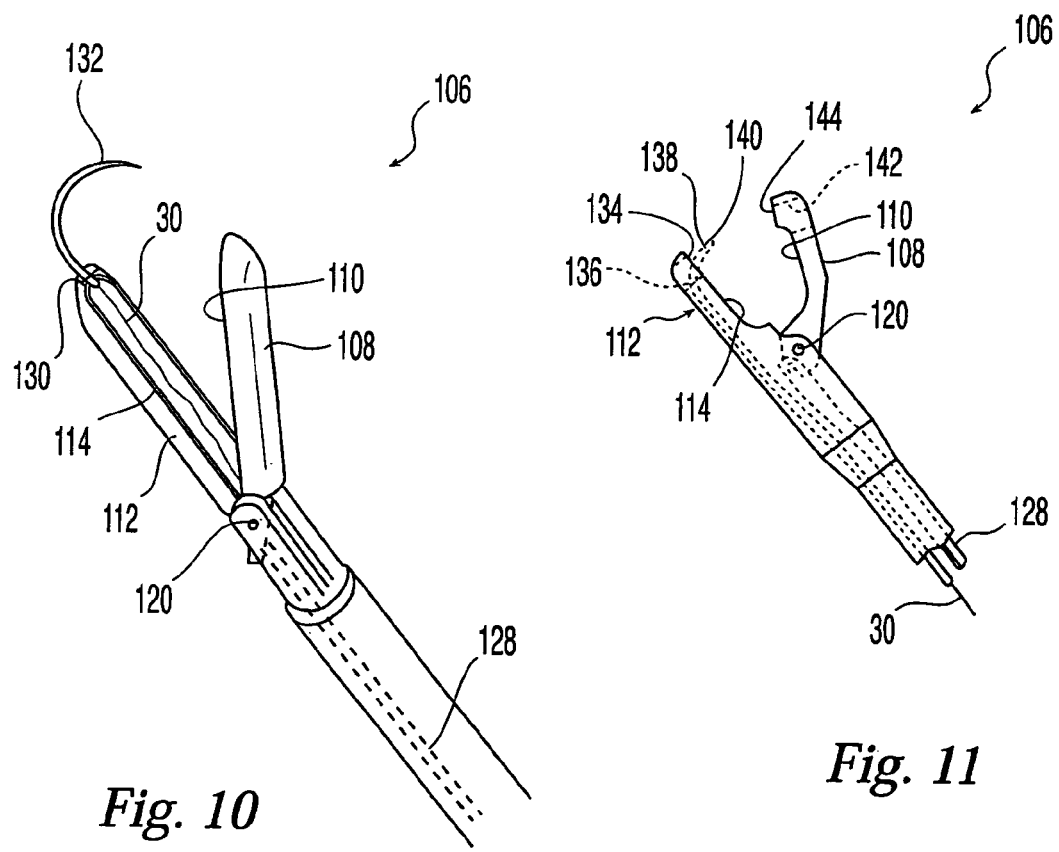
FIG. 10 shows one embodiment of jaws for the suture passer of FIG. 9.
Figure 11:
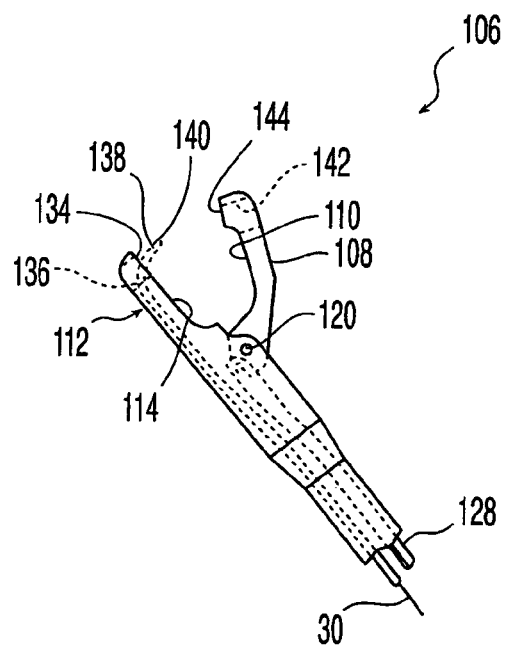
FIG. 11 shows another embodiment of jaws for the suture passer of FIG. 9.
Figure 12:
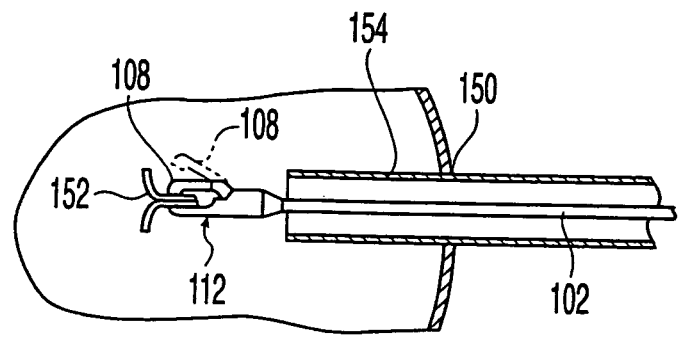
FIG. 12 shows the suture passer of FIG. 9 clamping the tissue to be sutured.
Figure 13:
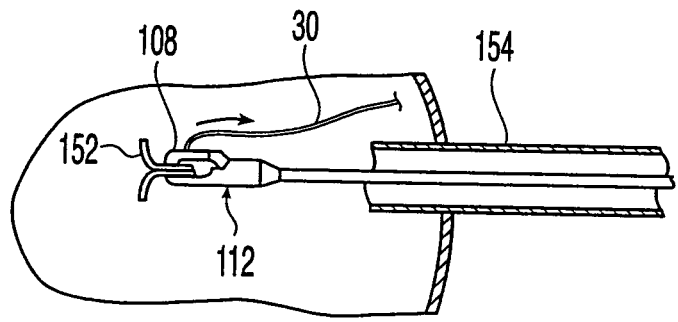
FIG. 13 shows the suture passer of FIG. 9 after the suture has passed through the tissue.

In an exemplary embodiment, handle 116 comprises first and second handles 122, 124, which are moveable with respect to each other and are operatively associated with first and second jaws 108, 112 so that movement of first and second handles 122, 124 moves first and second jaws 108, 112 between the open and closed positions. As shown, first and second handles 122, 124 are scissors-type handles, with first handle 122 rotatable toward second handle 124 about pivot point 126. First handle 122 is coupled to an end of an actuation rod 128. As best seen in FIGS. 10 and 11, the other end of actuation rod 128 is coupled to first jaw 108 so that squeezing of first and second handles 122, 124 results in axial movement of actuation rod 128 and, consequently, pivoting of first jaw 108 with respect to second jaw 112. Other handle mechanisms used for arthroscopic type instruments can be used. For example, U.S. Pat. No. 5,899,911, the contents of which are incorporated herein by reference, teaches a syringe-type handle and could be utilized on suture passer 100.

FIG. 10 also shows that second jaw 112 includes a clip 130 for holding suture needle 132. Suture 30 extends from suture needle 132 either along or within body 102. Alternatively, clip 130 can be located on first jaw 108. Other suitable retaining mechanisms for removeably securing needle 132 to one of first and second jaws 108, 112 can be used. U.S. Pat. No. 5,947,982, the contents of which are incorporated herein by reference, discloses jaw members capable of holding the needle so that the angular orientation of the needle can be varied. The use of such jaw members with suture passer 100 is also envisioned by the present invention.

FIG. 11 shows another embodiment of first and second jaws 108, 112. Second jaw 112 includes a wall 134 for engaging tissue to be sutured and a recess 136 in which is secured a hollow, tubular needle 138 having a cutting tip 140 to penetrate tissue to be sutured. Needle 138 can be curved such that the portion terminating at tip 140 extends substantially transverse from a portion of needle 138 secured in recess 136 and, thus extends substantially transverse from the plane of the ends of wall 134 of second jaw 112. First jaw 108 includes an aperture 142 therethrough aligned with needle 138 such that needle tip 140 will extend into the aperture when first and second jaws 108, 112 are closed. First jaw 108 has a surface 144 facing the surface of wall 134 of second jaw 112 such that tissue to be sutured can be clamped between surfaces 134 and 144 when first and second jaws 108, 112 are in the closed position.

As needle 138 is hollow, suture 30 can be fed therethrough, with the suture extending along or within body 30. Any number of known suture feed mechanisms can be used. An example of such a mechanism is taught by U.S. Pat. No. 4,957,498, the contents of which are incorporated herein by reference.

Use and operation of suture passer 100 will be described with reference to FIGS. 12-15. Suture passer 100 is inserted into the body through an incision or portal 150 in the skin and moved to tissue 152, which is to be sutured. Suture passer can be inserted through cannula 154 or suture passer 100 can be provided with a sharp tip to avoid the use of a cannula. Regardless, positioning of suture passer 100 can be monitored using conventional arthroscopic instruments that permit video viewing of the surgical site for inspection, diagnosis and surgery.

First and second jaws 108, 112 are moved to the open position by switching controller 118 to the appropriate position. This position can be such that first magnetic element 110, i.e. the electromagnet, is shut off so that first and second jaws 108, 112 swing open under the influence of a spring or other biasing member. Alternatively, controller 118 can be set in a position that causes the polarity of first magnetic element 110 to be such that magnetic repulsion between first and second magnetic elements 110, 114 causes first and second jaws 108, 112 to swing open. First and second jaws 108, 112 can also be opened by operating the conventional mechanism of first and second handles 122, 124. When first and second jaws 108, 112 are positioned on opposite sides of tissue 152, controller 118 is switched into a position such that magnetic attraction between first and second magnetic elements 110, 114 causes first and second jaws 108, 112 to move to the closed position. Tissue engaging surfaces 134 and 144 of first and second jaws 108, 112 clamp tissue 152 while needle 138 is forced through tissue 152 and into opening 142. Accordingly, suture passer 100 operates as a punch as needle 138 penetrates through tissue 152.

Although it is envisioned that the magnetic attraction alone could drive needle 138 through tissue 152, this magnetic attraction could be assisted by mechanical force, e.g. operating first and second handles 122, 124 to move first and second jaws 108, 112 toward the closed position. As previously noted, the desirability of this assistance depends upon a number of factors.

Figure 14:
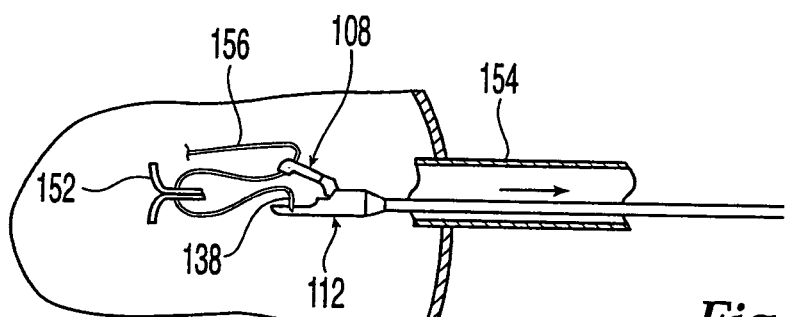
FIG. 14 shows the suture passer of FIG. 9 being withdrawn from the body.
Figure 15:
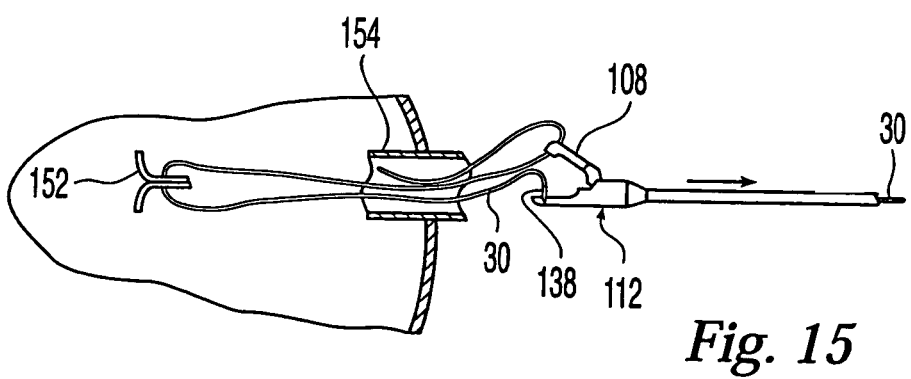
FIG. 15 shows the suture passer of FIG. 9 withdrawn from the body.

After first and second jaws 108, 112 are operated to punch needle 138 through tissue 152, suture 30 is forced through needle 138 to exit from tip 140 of needle 138 and pass through opening 142 in second jaw 112. Once a sufficient length of suture 30 material is fed through as shown in FIG. 14, first and second jaws 108, 112 are opened (either using controller 118 or handles 122, 124) to withdraw needle 138 back through tissue 152. Suture passer 100 is then moved away from tissue 152 causing a free end segment 156 of suture 30 to be folded back on itself with the edge of aperture 142 in second jaw 112 catching suture 30 to pull free end segment 156 out so that suture passer 100 can be withdrawn from the body leaving suture 30 in place through tissue 152 as shown in FIG. 15. With the ends of suture 30 outside the body, the surgeon in any conventional fashion can tie a knot, or other securing mechanisms can be used.

Figure 16:
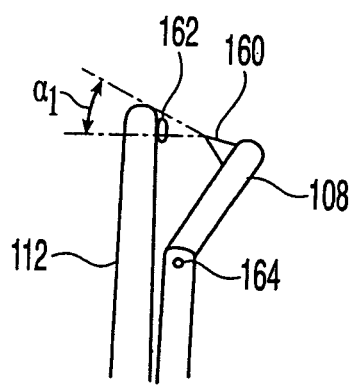
FIG. 16 shows another embodiment of jaws for the suture passer of FIG. 9.
Figure 17:
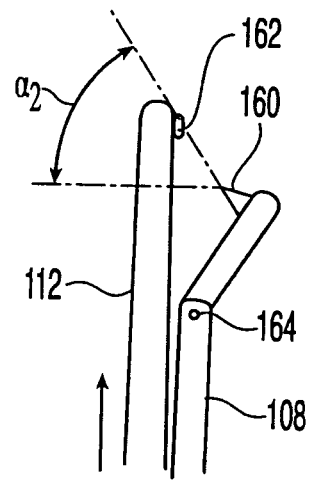
FIG. 17 shows the jaws of FIG. 16 with one jaw longitudinally moved with respect to the other jaw.

FIGS. 16 and 17 show another embodiment of first and second jaws 108, 112. First and second jaws 108, 112 are longitudinally moveable with respect to one another so that the angle at which needle 160 is inserted through the tissue can be varied. As shown in FIG. 16, magnetic element 162 on second jaw 112 lines up with needle 160 so that needle 160 would be inserted at an angle $\alpha_1$ that is close to zero degrees. In other words, needle 160 would enter the tissue substantially perpendicular to the plane of the tissue. In FIG. 17, first and second jaws 108, 112 have been moved with respect to one another so that magnetic element 162 would attract needle 160 to be inserted at an angle $\alpha_2$ that is greater than $\alpha_1$.

There are a number of different mechanisms to achieve relative longitudinal movement of first and second jaws 108, 112. For example, first jaw 108 can be provided with a pivot point 164 to effect movement of first and second jaws 108, 112 between the open and closed positions. This allows second jaw 112 to be moveable with respect to first jaw 108 without hindering opening and closing of first and second jaws 108, 112. This movement of second jaw 112 can be controlled with any known means located on the body of the suture passer.

Figure 18:
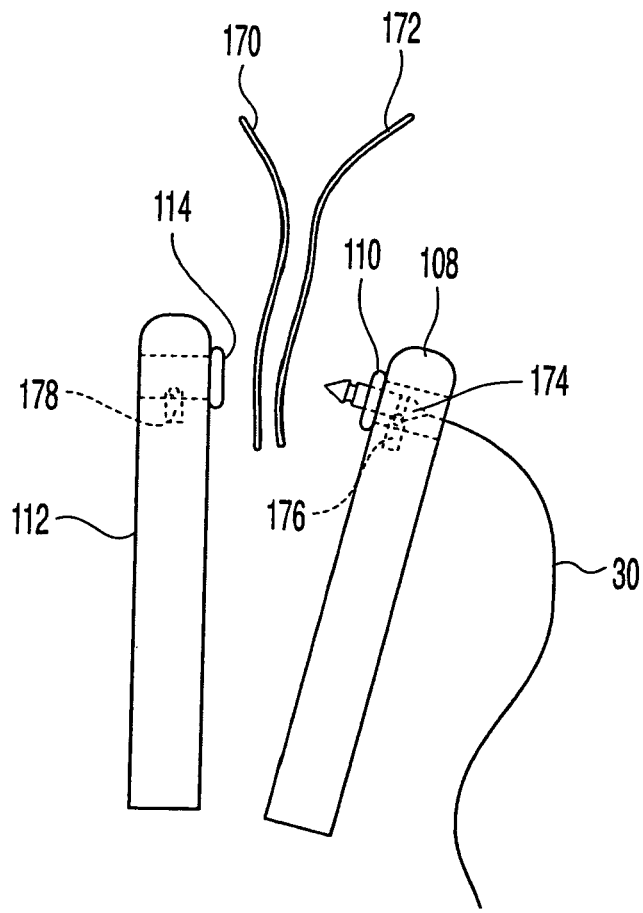
FIG. 18 shows another embodiment of jaws for the suture passer of FIG. 9.

In the embodiment of FIG. 18, both first magnetic element 110 on first jaw 108 and second magnetic element 114 on second jaw 112 are magnets. As first and second jaws 108, 112 are positioned to be proximal to tissue sections 170, 172, first magnetic element 110 is activated so that implant 174 is attached to first jaw 108. Although the magnetic interaction between first magnetic element 110 and implant 174 may be sufficient to secure implant 174 to first jaw 108, first jaw 108 can be provided with a mechanical stop 176 to further secure implant 174 to first jaw 108. Mechanical stop 176 is shown as a ball detent mechanism that automatically activates when implant 174 is inserted. However, mechanical stop 176 can be configured to activate when first magnetic element 110 is activated, or a separate triggering mechanism for mechanical stop 176 can be provided.

Figure 19:
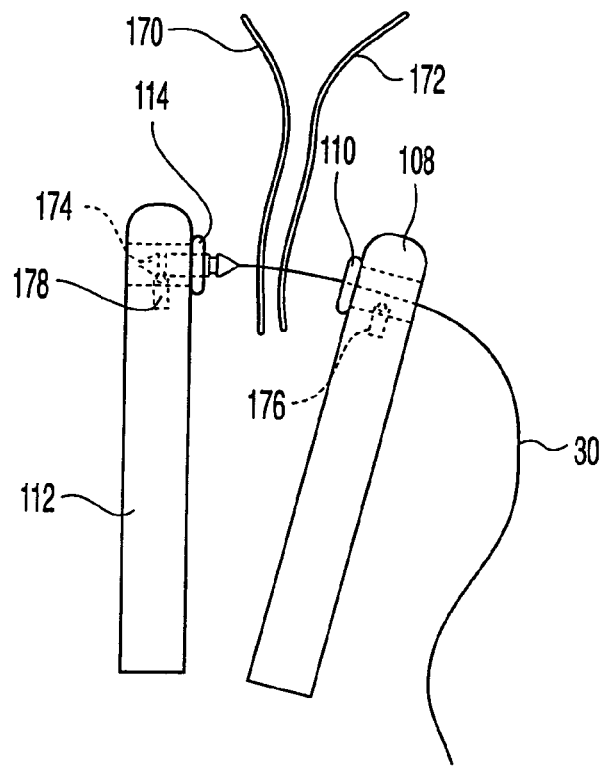
FIG. 19 shows the jaws of FIG. 18 with the implant passed once through the tissue.
Figure 20:
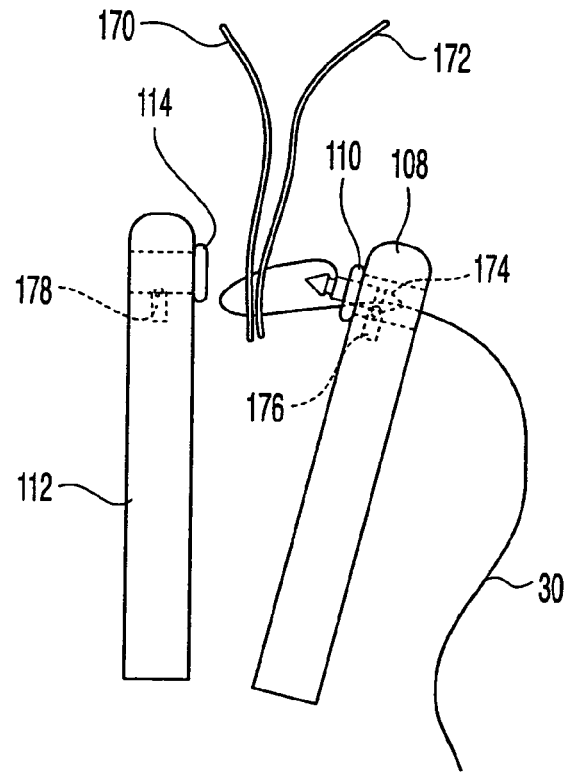
FIG. 20 shows the jaws of FIG. 18 with the implant passed twice through the tissue.

When first and second jaws 108, 112 are properly positioned, first magnetic element 110 is deactivated and second magnetic element 114 is activated to pass implant 174 through tissue sections 170, 172 as shown in FIG. 19. Although the magnetic interaction between second magnetic element 114 and implant 174 may be sufficient to secure implant 174 to second jaw 112, second jaw 112 can be provided with a mechanical stop 178 (also shown as a ball detent mechanism) to further secure implant 174 to second jaw 112. Mechanical stop 178 can also be configured to activate when second magnetic element 114 is activated, or a separate triggering mechanism for mechanical stop 178 can be provided. With implant 174 secured to second jaw 112, first and second jaws 108, 112 can be moved to draw suture 30 tautly through tissue sections 170, 172. This process brings tissue sections 170, 172 into apposition. As shown in FIG. 20, the process of alternating the activation and deactivation of first and second magnetic elements 110, 114 can be repeated as desired to move implant 174 back and forth across tissue sections 170, 172, resulting in suturing of tissue sections 170, 172. As illustrated with respect to the other embodiments, other manipulations of implant 174 and suture 30 are possible with the present invention.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed:

1. An apparatus configured to pass a suture through tissue, said apparatus comprising:
   an elongate body configured to be inserted at least partially inside a body of a patient, the elongate body defined about a longitudinal axis, the elongate body having a magnetically operable distal end with first and second members, the first member configured to be movable relative to the second member;
   a biasing member configured to bias the distal end first member in a closed position relative to the distal end second member;
   a handle coupled to the elongate body;
   a needle coupled to the second member, wherein the needle is positioned to extend at least partially into an aperture formed in the first member;
   a magnetizable material disposed in or on at least a portion of the first or second member;

an electromagnet disposed in or on at least the other of the first or second member, wherein the first member is configured to be attracted or repelled relative to the second member by a magnetic field created by the electromagnet such that the first and second members are configured to move to a closed position to retain a portion of tissue therebetween; and a controller directly mounted on the handle, the controller configured to control the electromagnet.

2. The apparatus of claim 1, wherein the magnetizable material includes a permanent magnet.

3. The apparatus of claim 1, wherein the magnetizable material includes a second electromagnet.

4. The apparatus of claim 1, wherein the controller is configured to adjust at least one of strength and polarity of the electromagnet to facilitate at least one of opening and closing of the first and second members.

5. The apparatus of claim 4, wherein the controller is configured to reverse said polarity of the electromagnet to open the first and second members.

6. The apparatus of claim 1, wherein the controller is further configured to at least one of turn on and turn off the electromagnet.

7. The apparatus of claim 1, wherein the electromagnet is configured to selectively adjust the position of a tissue section or an implant by changing the magnetic field.

8. The apparatus of claim 1, further comprising a suture configured to connect with the needle.

9. The apparatus of claim 1, wherein the first and second engaging member is configured to be positionable adjacent to a tissue section.

10. The apparatus according to claim 1, wherein said electromagnet is configured to create a magnetic field that attracts or repels said magnetizable material.

11. The apparatus according to claim 1, wherein said magnetizable material creates a second magnetic field.

12. The apparatus according to claim 1, wherein said electromagnet is configured to urge the needle into at least a portion of a tissue section.

13. The apparatus according to claim 1, wherein said magnetizable material includes iron.

14. The apparatus of claim 1, wherein a location or direction of said magnetic field is adjustable.

15. The apparatus of claim 1, wherein the first and second members include electromagnets.

16. The apparatus of claim 1, wherein said electromagnet is configured to be selectively activatable, deactivatable, or adjustable.

17. The apparatus according to claim 1, further comprising a holder connected to said first member for releasably holding the needle.

18. The apparatus according to claim 1, wherein the elongate body is substantially cylindrical.

19. An apparatus configured to pass a suture through tissue, said apparatus comprising:
an elongate body defined about a longitudinal axis;
a handle coupled to the elongate body;
a first member;
a second member coupled to the first member at a pivot at or near a distal end of the elongate body, the first member configured to be movable relative to the second member;
a needle coupled to the second member;
a magnetizable material disposed in or on the first member, said magnetizable material configured to attract said needle; and a controller directly mounted on the handle and configured to control the electromagnet.

20. The apparatus according to claim 19, wherein said magnetizable material includes a permanent magnet.

21. The apparatus according to claim 19, wherein said magnetizable material includes iron.

22. The apparatus according to claim 19, further comprising a magnetic field generator configured to move the first member relative to the second member when actuated.

23. The apparatus according to claim 22, wherein said magnetic field generator is configured to repel said magnetizable material to spread said first member relative to said second member.

24. The apparatus according to claim 22, wherein the magnetic field generator includes an electromagnet.

25. The apparatus according to claim 24, wherein said electromagnet is configured to be selectively activatable, deactivatable, or adjustable.

26. The apparatus according to claim 19, further comprising a biasing member connected to said first member and said second member to urge the first and second members toward or away from each other.

27. The apparatus according to claim 19, wherein a location or direction of the magnetic field is adjustable.

28. The apparatus according to claim 19, further comprising a holder connected to said first member for releasably holding the needle.

29. The apparatus according to claim 19, wherein the needle includes a magnetic component.

30. The apparatus according to claim 19, wherein the elongate body is substantially cylindrical.

31. An apparatus comprising:
an elongate body about a longitudinal axis;
a handle coupled to the elongate body;
a first portion and a second portion at or near a distal end of the elongate body, the first portion configured to be attracted and repelled by a magnetic field;
the first or second portion including a magnetizable material;
the other of the first or second portion including an electromagnet; a needle releasably connected to the first or second portion;
a biasing member configured to bias the distal end first portion in a closed position relative to the distal end second portion; and
a controller directly mounted on the handle, the controller electrically coupled to the electromagnet and configured to control the electromagnet wherein the controller is configured to at least power the electromagnet on and off.

32. The apparatus of claim 31, wherein the magnetizable material includes a permanent magnet or a second electromagnet.

33. The apparatus of claim 31, wherein the first and second portions include electromagnets.

34. The apparatus of claim 31, wherein a location or direction of the magnetic field is adjustable.

35. The apparatus of claim 31, wherein the strength or polarity of the electromagnet is adjustable by changing a current to the electromagnet by the controller.

36. The apparatus of claim 31, wherein the polarity is reversible.

37. The apparatus of claim 31, wherein the first or section portion is configured to adjust the position of a tissue section or the needle.

38. The apparatus of claim 31, wherein the first and second portions include electromagnets.

39. The apparatus of claim 31, wherein said electromagnet is configured to be at least one of selectively activatable, deactivatable, and adjustable.

40. The apparatus according to claim 31, further comprising a suture connected to the needle.

41. The apparatus according to claim 31, wherein the elongate body is substantially cylindrical.

* * * * *